US009364578B2

(12) United States Patent
Zhu et al.

(10) Patent No.: US 9,364,578 B2
(45) Date of Patent: *Jun. 14, 2016

(54) HEMOSTATIC AGENT FOR TOPICAL AND INTERNAL USE

(71) Applicant: Loma Linda University Medical Center, Loma Linda, CA (US)

(72) Inventors: Yong Hua Zhu, Redlands, CA (US); Chang Zheng Yang, Nanjing (CN); Wolff M. Kirsch, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/193,416

(22) Filed: Feb. 28, 2014

(65) Prior Publication Data

US 2014/0178446 A1 Jun. 26, 2014

Related U.S. Application Data

(63) Continuation of application No. 11/061,243, filed on Feb. 18, 2005, now Pat. No. 8,703,176.

(60) Provisional application No. 60/547,257, filed on Feb. 23, 2004, provisional application No. 60/638,865, filed on Dec. 22, 2004, provisional application No. 60/547,166, filed on Feb. 23, 2004.

(51) Int. Cl.
*A61F 13/00* (2006.01)
*A61K 9/70* (2006.01)
*A61L 15/28* (2006.01)
*A61B 17/00* (2006.01)

(Continued)

(52) U.S. Cl.
CPC .............. *A61L 15/28* (2013.01); *A61B 17/0057* (2013.01); *A61B 17/06166* (2013.01); *A61L 26/0023* (2013.01); *A61B 2017/00526* (2013.01); *A61B 2017/00623* (2013.01); *A61B 2017/00884* (2013.01); *A61B 2017/00898* (2013.01); *A61L 2400/04* (2013.01)

(58) Field of Classification Search
CPC ............................. A61K 8/0208; A61L 15/28
See application file for complete search history.

(56) References Cited

U.S. PATENT DOCUMENTS 3,390,681 A 7/1968 Kurtz
3,533,940 A 10/1970 Peniston et al.
(Continued)

FOREIGN PATENT DOCUMENTS

EP 1152013 A1 11/2001
KR 20010079260 A 9/2001
(Continued)

OTHER PUBLICATIONS

Drake, J. F. "Fate of Porous Starch Microbeads in Mammalian Tissues", Nov. 18, 2002.
(Continued)

*Primary Examiner* — Benjamin Packard
(74) *Attorney, Agent, or Firm* — Knobbe Martens Olson & Bear, LLP

(57) ABSTRACT

This invention relates to deployable hemostatic materials comprising chitosan fibers. The hemostatic materials are suitable for use in sealing or controlling active bleeding from artery and vein lacerations and punctures, and for controlling oozing from tissue.

13 Claims, 10 Drawing Sheets

(51) Int. Cl.
*A61B 17/06* (2006.01)
*A61L 26/00* (2006.01)

(56) References Cited

U.S. PATENT DOCUMENTS

| | | | |
|---|---|---|---|
| 4,394,373 | A | 7/1983 | Malette |
| 4,452,785 | A | 6/1984 | Malette |
| 4,532,134 | A | 7/1985 | Malette |
| 5,836,970 | A | 11/1998 | Pandit |
| 5,885,609 | A | 3/1999 | Amiji |
| 6,060,461 | A | 5/2000 | Drake |
| 6,465,626 | B1 | 10/2002 | Watts et al. |
| 6,596,296 | B1 * | 7/2003 | Nelson et al. ............ 424/426 |
| 6,806,260 | B1 | 10/2004 | Hirofumi et al. |
| 7,098,194 | B2 | 8/2006 | Chenite et al. |
| 7,252,837 | B2 | 8/2007 | Guo et al. |
| 2002/0197032 | A1 | 12/2002 | Cochrun et al. |
| 2004/0054346 | A1 | 3/2004 | Zhu et al. |

FOREIGN PATENT DOCUMENTS

| | | |
|---|---|---|
| KR | 20010096018 A | 11/2001 |
| WO | WO 01/24840 A | 4/2001 |
| WO | WO 01/41820 | 6/2001 |
| WO | WO 2005/002510 | 1/2005 |
| WO | WO 2005/041811 | 5/2005 |

OTHER PUBLICATIONS

Ereth et al., "Efficacy of Microporous Polysaccharide Hemospheres on Liver Punch biopsies in Porcine Model", Anesthesiology Abstracts of Scientific Papers Annual Meeting, No. 2003, 2003, Abstract No. A-153 URL, Abstract XP002476226 & 2003 Annual Meeting of the American Society of Anesthesiologists, San Francisco, CA, Oct. 11-15, 2003.

Everaers, et al. "Rheology and Microscopic Topology of Entangled Polymeric Liquids", Science, vol. 202, Feb. 6, 2004.

Heller et al., "Alginate/chitosan microporous microspheres for the controlled release of proteins and antigens", Proceedings of the Controlled Release Society, No. 23, pp. 269-270, 1996.

Medafor, Ereth et al. "Microporous Polysaccharide Hemospheres Provide Effective Topical Hemostasis in a Human Modified Bleeding Time Inclusion Model", Hemoostatic Polymer Technologies, Sep. 2002.

Pathology Report, "The Wound Healing Effects in Porcine Skin Grafts After Application of Microporous Polysaccharide Hemospheres (MPH)", Aug. 14, 2002, Medafor, Inc., Minneapolis, MN.

Tan et al., "Effectiveness of microporous polysaccharide hemospheres for achieving hemostasis in mohs micrograph surgery", Dermatologic Surgery: Official Publication for American Society for Dermatologic Surgery, Jun. 2004, vol. 30, No. 6, pp. 908-914.

Wang et al., "Studies on hepatic arterial embolization with cisplatin-chitosan-microspheres in dogs" Abstract XP002476227, Medline Database Accession No. NLM8712014, Acta Pharmaceutica Sinica, Dec. 1995, vol. 30, No. 12, pp. 891-895.

Ziauddin, et al. "Use of Microporous Polysaccharide Particles in Prolonged Vascular Access Bleeding After Hemodialysis", American Society of Nephrology, Friday, Nov. 1, 2002, Poster Board No. F-P0835.

* cited by examiner

HEMOSTATIC AGENT FOR TOPICAL AND INTERNAL USE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 11/061,243, filed on Feb. 18, 2005, which claims the benefit of U.S. Provisional Application No. 60/638,865 filed Dec. 22, 2004, U.S. Provisional Application No. 60/547,166 filed Feb. 23, 2004, and U.S. Provisional Application No. 60/547,257 filed Feb. 23, 2004. Each of the aforementioned applications is incorporated by reference herein in its entirety, and each is hereby expressly made a part of this specification.

FIELD OF THE INVENTION

This invention relates to deployable hemostatic materials comprising chitosan fibers. The hemostatic materials are suitable for use in sealing or controlling active bleeding from artery and vein lacerations and punctures, and for controlling oozing from tissue.

BACKGROUND OF THE INVENTION

Surgical procedures and traumatic injuries are often characterized by massive blood loss. Conventional approaches such as manual pressure, cauterization, or sutures may be time consuming and are not always effective in controlling bleeding.

Over the years, a number of topical hemostatic agents have been developed to control bleeding during surgical procedures and to control bleeding resulting from traumatic injury. Some agents such as collagen-based powders, sponges, or cloths are of a particulate nature. Particulate hemostatic agents provide a lattice for natural thrombus formation, but are unable to enhance this process in coagulopathic patients. Microfibrillar collagen, a particulate hemostatic agent, comes in powder form and stimulates the patient's intrinsic hemostatic cascade. However, this product has been reported to embolize and induce a localized inflammatory response if used during cardiopulmonary bypass. Pharmacologically-active agents such as thrombin can be used in combination with a particulate carrier, for example, as in a gelfoam sponge or powder soaked in thrombin. Thrombin has been used to control bleeding on diffusely bleeding surfaces, but the lack of a framework onto which the clot can adhere has limited its use. The autologous and allogenic fibrin glues can cause clot formation, but do not adhere well to wet tissue and have little impact on actively bleeding wounds.

SUMMARY OF THE INVENTION

A hemostatic material that is bioabsorbable, that provides superior hemostasis, and that can be fabricated into a variety of forms suitable for use in controlling bleeding from a variety of wounds is desirable. In addition the hemostatic material that is suitable for use in both surgical applications as well as in field treatment of traumatic injuries is also desirable. For example, in vascular surgery, bleeding is particularly problematic. In cardiac surgery, the multiple vascular anastomoses and cannulation sites, complicated by coagulopathy induced by extracorporeal bypass, can result in bleeding that can only be controlled by topical hemostats. Rapid and effective hemostasis during spinal surgery, where control of osseous, epidural, and/or subdural bleeding or bleeding from the spinal cord is not amenable to sutures or cautery, can minimize the potential for injury to nerve roots and reduce the procedure time. In liver surgery, for example, live donor liver transplant procedures or removal of cancerous tumors, there is a substantial risk of massive bleeding. An effective hemostatic material can significantly enhance patient outcome in such procedures. Even in those situations where bleeding is not massive, an effective hemostatic material can be desirable, for example, in dental procedures such as tooth extractions, as well as the treatment of abrasions, burns, and the like. In neurosurgery, oozing wounds are common and are difficult to treat.

Accordingly, in a first aspect, a hemostatic material is provided, the material comprising chitosan fibers, wherein the chitosan has a molecular weight of about 1100 kDa or greater, and a degree of acetylation of about 90% or greater.

In a preferred embodiment of the first aspect, the hemostatic material comprises a puff or a fleece.

In a preferred embodiment of the first aspect, the hemostatic material comprises a nonwoven fabric or a woven fabric.

In a preferred embodiment of the first aspect, the hemostatic material comprises a nonwoven fabric having a rough side and a smooth side.

In a preferred embodiment of the first aspect, the hemostatic material comprises a nonwoven fabric wherein both sides are rough.

In a preferred embodiment of the first aspect, the hemostatic material comprises a plurality of chitosan fiber layers.

In a preferred embodiment of the first aspect, the chitosan fibers have been treated with an acetic acid solution.

In a preferred embodiment of the first aspect, the chitosan fibers have been treated with glacial acetic acid.

In a second aspect, a process for preparing a hemostatic material comprising chitosan fibers is provided, wherein the chitosan has a molecular weight of about 1100 kDa or greater, and a degree of acetylation of about 90% or greater, the process comprising providing a first chitosan fiber layer; applying a weak acid to the first chitosan fiber layer; and placing a second chitosan fiber layer atop the first chitosan fiber layer, whereby a hemostatic material is obtained.

In a preferred embodiment of the second aspect, the steps are repeated at least once.

In a preferred embodiment of the second aspect, the process further comprises the step of heating the hemostatic material, whereby a liquid is vaporized from the hemostatic material.

In a preferred embodiment of the second aspect, the process further comprises compressing the hemostatic material between a first surface and a second surface; and heating the hemostatic material, whereby a dry hemostatic material is obtained.

In a preferred embodiment of the second aspect, the weak acid comprises an acetic acid solution.

In a preferred embodiment of the second aspect, the weak acid comprises glacial acetic acid.

In a preferred embodiment of the second aspect, the weak acid comprises a solution of acetic acid having a pH of from about 3.0 to about 4.5.

In a third aspect, a method of treating a wound is provided, the method comprising the step of applying a hemostatic material to the wound, whereby bleeding or oozing is controlled, the hemostatic material comprising chitosan fibers, wherein the chitosan has a molecular weight of about 1100 kDa or greater, and a degree of acetylation of about 90% or greater.

In a preferred embodiment of the third aspect, the hemostatic material is in a form selected from the group consisting of a puff, a sponge, and a fabric.

In a preferred embodiment of the third aspect, the wound is selected from the group consisting of a tumor bed, a liver wound, and a brain wound.

In a preferred embodiment of the third aspect, the wound is selected from the group consisting of an arterial puncture wound, a venous puncture wound, arterial laceration wound, and a venous laceration wound.

In a preferred embodiment of the third aspect, the chitosan fibers have been treated with glacial acetic acid.

DETAILED DESCRIPTION OF THE PREFERRED EMBODIMENT

Figure 1:
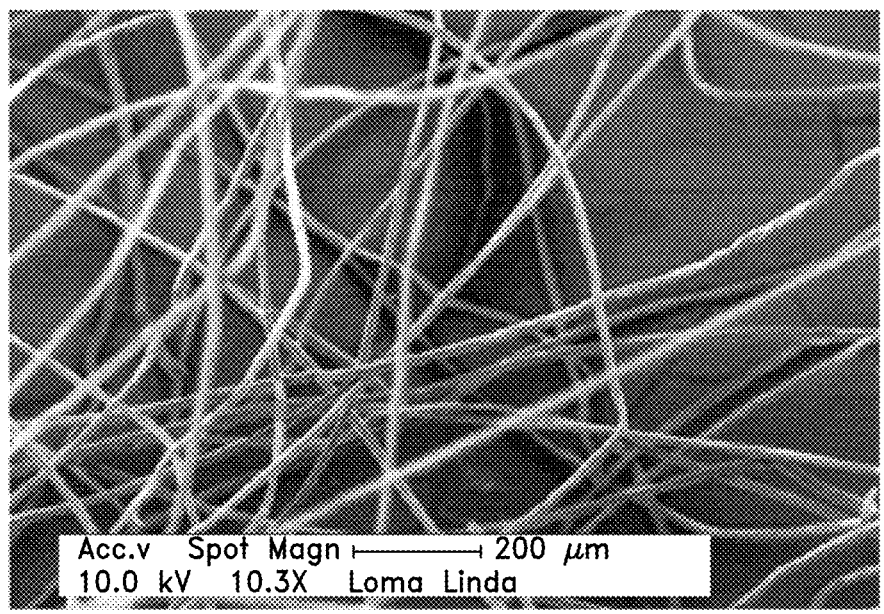
FIG. 1 provides a scanning electron micrograph (SEM) image of a chitosan fleece.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Hemostasis

Hemostasis is the arrest of bleeding, whether by normal vasoconstriction, by an abnormal obstruction, or by coagulation or surgical means. Hemostasis by coagulation is dependent upon a complex interaction of plasma coagulation and fibrinolytic proteins, platelets, and the blood vasculature. There are three categories of hemostasis: primary hemostasis, secondary hemostasis, and tertiary hemostasis.

Primary hemostasis is defined as the formation of the primary platelet plug. It involves platelets, the blood vessel wall and von Willebrand factor. Injury to the blood vessel wall is initially followed by vasoconstriction. Vasoconstriction not only retards extravascular blood loss, but also slows local blood flow, enhancing the adherence of platelets to exposed subendothelial surfaces and the activation of the coagulation process. The formation of the primary platelet plug involves platelet adhesion followed by platelet activation then aggregation to form a platelet plug.

In platelet adhesion, platelets adhere to exposed subendothelium. In areas of high shear rate, such as in the microvasculature, this is mediated by von Willebrand factor (vWf), which binds to glycoprotein Ib-IX in the platelet membrane. In areas of low shear rate, such as in the arteries, fibrinogen mediates the binding of platelets to the subendothelium by attaching to a platelet receptor. The adhesion of platelets to the vessel wall activates them, causing the platelets to change shape, to activate the collagen receptor on their surface, and to release alpha and dense granule constituents. The activated platelets also synthesize and release thromboxane A2 and platelet activating factor, which are potent platelet aggregating agonists and vasoconstrictors.

Platelet aggregation involves the activation, recruitment, and binding of additional platelets, which bind to the adhered platelets. This process in promoted by platelet agonists such as thromboxane 2, PAF, ADP, and serotonin. This activation is enhanced by the generation of thrombin, another platelet agonist, through the coagulation cascade. Platelet aggregation is mediated primarily by fibrinogen, which binds to glycoprotein IIb/IIIa on adjacent platelets. This aggregation leads to the formation of the primary platelet plug, is stabilized by the formation of fibrin.

In secondary hemostasis, fibrin is formed through the coagulation cascade, which involves circulating coagulation factors, calcium, and platelets. The coagulation cascade involves three pathways: intrinsic, extrinsic, and common.

The extrinsic pathway involves the tissue factor and factor VII complex, which activates factor X. The intrinsic pathway involves high-molecular weight kininogen, prekallikrein, and factors XII, XI, IX and VIII. Factor VIII acts as a cofactor (with calcium and platelet phospholipid) for the factor IX-mediated activation of factor X. The extrinsic and intrinsic pathways converge at the activation of factor X. The common pathway involves the factor X-mediated generation of thrombin from prothrombin (facilitated by factor V, calcium and platelet phospholipid), with the production of fibrin from fibrinogen.

The main pathway for initiation of coagulation is the extrinsic pathway (factor VII and tissue factor), while the intrinsic pathway acts to amplify the coagulation cascade. The coagulation cascade is initiated by the extrinsic pathway with the generation/exposure of tissue factor. Tissue factor is expressed by endothelial cells, subendothelial tissue and monocytes, with expression being upregulated by cytokines. Tissue factor then binds to factor VII and this complex activates factor X. Factor X, in the presence of factor V, calcium and platelet phospholipid, then activates prothrombin to thrombin. This pathway is rapidly inhibited by a lipoprotein-associated molecule, called tissue factor pathway inhibitor. However, the small amount of thrombin generated by this pathway activates factor XI of the intrinsic pathway, which amplifies the coagulation cascade.

The coagulation cascade is amplified by the small amounts of thrombin generated by the extrinsic pathway. This thrombin activates the intrinsic pathway by activation of factors XI and VIII. Activated factor IX, together with activated factor VIII, calcium, and phospholipid, referred to as tenase complex, amplify the activation of factor X, generating large amounts of thrombin. Thrombin, in turn, cleaves fibrinogen to form soluble fibrin monomers, which then spontaneously polymerize to form the soluble fibrin polymer. Thrombin also activates factor XIII, which, together with calcium, serves to cross-link and stabilize the soluble fibrin polymer, forming cross-linked fibrin.

Tertiary hemostasis is defined as the formation of plasmin, which is the main enzyme responsible for fibrinolysis. At the same time as the coagulation cascade is activated, tissue plasminogen activator is released from endothelial cells. Tissue plasminogen activator binds to plasminogen within the clot, converting it into plasmin. Plasmin lyses both fibrinogen and fibrin in the clot, releasing fibrin and fibrinogen degradation products.

The preferred embodiments provide compositions and materials that react with the hemostatic system to treat or prevent bleeding. In particular, the compositions and materials of preferred embodiments result in coagulation of blood.

Effective delivery of hemostatic agents to wounds is particularly desirable in the treatment of injuries characterized by arterial or venous bleeding, as well as in surgical procedures where the control of bleeding can become problematic, e.g., large surface areas, heavy arterial or venous bleeding, oozing wounds, and organ laceration/resectioning. The compositions and materials of preferred embodiments can possess a number of advantages in delivery of hemostatic agents to wounds, including but not limited to ease of application and removal, bioadsorption potential, suturability, antigenicity, and tissue reactivity.

Depending upon the nature of the wound and the treatment method employed, the devices of preferred embodiments can employ different forms. For example, a puff, fleece, or sponge form can be preferable for controlling the active bleeding from artery or vein, or for internal bleeding during laparoscopic procedures. In neurosurgery where oozing brain wounds are commonly encountered, a sheet form of the hemostatic material can be preferred. Likewise, in oncological surgery, especially of the liver, it can be preferred to employ a sheet form or sponge form of the hemostatic material, which is placed in or on the tumor bed to control oozing. In dermatological applications, a sheet form can be preferred. In closing punctures in a blood vessel, a puff form is generally preferred. A suture form, such as a microsuture or a macrosuture, can be preferred in certain applications. Despite differences in delivery and handling characteristic of the different forms, the devices are effective in deploying hemostatic agents to an affected site and to rapidly initiate hemostatic plug formation through platelet adhesion, platelet activation, and blood coagulation.

In preferred embodiments a hemostatic agent comprising chitosan fibers is employed. An auxiliary hemostatic agent, such as bioabsorbable microporous polysaccharide microspheres, can be deposited upon the chitosan fibers. However, any other suitable auxiliary hemostatic agents can be employed.

Hemostatic Substrate

Any suitable hemostatic substrate can be employed as a support for the hemostatic agents of preferred embodiments. However, in a particularly preferred embodiment, the hemostatic substrate comprises chitosan. Chitosan is obtained from chitin, a widely available biopolymer obtained principally from shrimp and crab shell waste. Chitosan is the main derivative of chitin, and is the collective term applied to deacetylated chitins in various stages of deacetylation and depolymerization. The chemical structure of chitin and chitosan is similar to that of cellulose. The difference is that instead of the hydroxyl group as is bonded at C-2 in each D-glucose unit of cellulose, there is an acetylated amino group (—NHCOCH$_3$) at C-2 in each D-glucose unit in chitin and an amino group at C-2 in each D-glucose unit of chitosan.

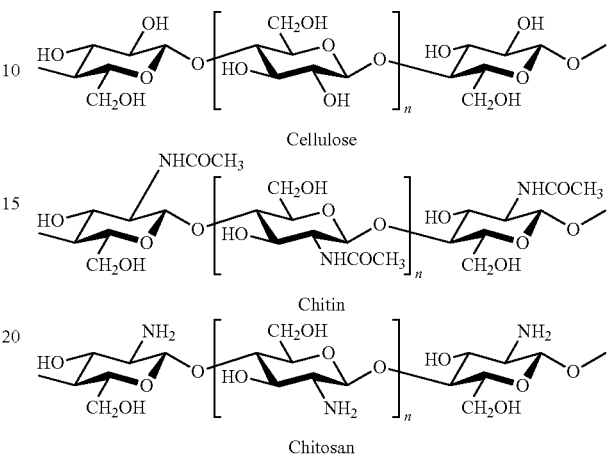

Chitin and chitosan are both nontoxic, but chitosan is used more widely in medical and pharmaceutical applications than chitin because of its good solubility in acid solution. Chitosan has good biocompatibility and is biodegradable by chitosanase, papain, cellulase, and acid protease. Chitosan exhibits anti-inflammatory and analgesic effects, and promotes hemostasis and wound healing. Chitosan has also been used as a hemostatic agent in surgical treatment and wound protection. The hemostatic effect of chitosan has been described in U.S. Pat. No. 4,394,373.

A single hemostatic substrate or combination of hemostatic substrates can be employed. Different substrate forms can be preferred, for example, puff, fleece, fabric or sheet, sponge, suture, or powder. A homogeneous mixture of different substrate-forming materials can be employed, or composite substrates can be prepared from two or more different formed substrates. A preferred composite comprises chitosan and collagen.

A particularly preferred source of chitin for use in preparing chitosan fleece is crab shell. Chitin prepared from crab shell generally exhibits a molecular weight that is much higher than the molecular weight of chitin made from shrimp shell. Crab shell chitin also generally exhibits a higher degree of deacetylation than shrimp shell chitin. Crab shell chitin typically exhibits an average molecular weight of from about 600,000 to 1.3 million molecular weight. The degree of deacetylation is generally more than 90%, which can contribute to the higher molecular weight observed.

Preferred chitosan for use in preparing chitosan fiber has a molecular weight of greater than about 600, 650, 700, 750, 800, 850, 900, 950, 1000, 1100, 1200, 1300, 1400, or 1500 kDa or more; more preferably from about 600, 650, 700, 750, 800, 925, 850, 875, 900, 925, 950, 975, 1000, 1025, 1050, or 1075 kDa to about 1500 kDa; and most preferably from about 1100, 1125, 1150, 1175, 1200, 1225, 1250, or 1275 kDA to about 1300, 1325, 1350, 1375, 1400, 1425, 1450, or 1475 kDa. The chitosan preferably has a degree of acetylation of about 90, 91, 92, 93, 94, 95, 96, 97, 98, or 99% or greater, more preferably from about 90.0, 90.5, 91.0, 91.5, or 92.0% to about 92.5, 93.0, 93.5, 94.0, 94.5, or 95.0%.

While chitosan is generally preferred for use as a substrate, other suitable substrates can also be employed. These substrates are preferably bioabsorbable hydrophilic materials that can be fabricated into a desired form (fiber, sponge, matrix, powder, sheet, suture, and/or puff).

Other suitable substrates include a synthetic absorbable copolymer of glycolide and lactide. This copolymer is marketed under the trade name VICRYL™ (a Polyglactin 910 manufactured by Ethicon, a division of Johnson & Johnson in Somerset, N.J.). It is absorbed though enzymatic degradation by hydrolysis.

Gelatin sponge is an absorbable, hemostatic sponge used in surgical procedures with venous and oozing bleeding. The sponge adheres to the bleeding site and absorbs approximately forty five times its own weight. Due to the uniform porosity of the gelatin sponge, blood platelets are caught within its pores, activating a coagulation cascade. Soluble fibrinogen transforms into a net of insoluble fibrin, which stops the bleeding. When implanted into the tissue, the gelatin sponge is absorbed within three to five weeks.

Polyglycolic acid is a synthetic absorbable polymer also suitable for use as a substrate. Polyglycolic acid is absorbed within a few months post-implantation due to its greater hydrolytic susceptibility.

Polylactide is prepared from the cyclic diester of lactic acid (lactide) by ring opening polymerization. Lactic acid exists as two optical isomers or enantiomers. The L-enantiomer occurs in nature, a D,L racemic mixture results from the synthetic preparation of lactic acid. Fibers spun from polymer derived from the L-enantiomer have high crystallinity when drawn whereas fibers derived from the racemic mixture are amorphous. Crystalline poly-L-lactide is generally more resistant to hydrolytic degradation than the amorphous DL form, but can be increased by plasticization with triethyl citrate, however the resulting product is less crystalline and more flexible. The time required for poly-L-lactide to be absorbed by the body is relatively long compared to other bioabsorbable materials. High molecular weight poly-L-lactide polymers can be prepared, and the fibers with large tensile strength obtained.

Poly(lactide-co-glycolide) polymers are also suitable substrates. These copolymers are amorphous between the compositional range 25 to 70 mole percent glycolide. Pure polyglycolide is about 50% crystalline, whereas pure poly-L-lactide is about 37% crystalline.

Polydioxanone can be fabricated into fibers to form a suitable substrate. Polycaprolactone, synthesized from e-caprolactone, is a semi-crystalline polymer absorbed very slowly in vivo. Copolymers of e-caprolactone and L-lactide are elastomeric when prepared from 25% e-caprolactone, 75% L-lactide and rigid when prepared from 10% e-caprolactone, 90% L-lactide. Poly-b-hydroxybutyrate is a biodegradable polymer that occurs in nature, that can easily be synthesized in vitro, and that is melt processable. Copolymers of hydroxybutyrate and hydroxyvalerate have more rapid degradation than can be achieved with pure poly-b-hydroxybutyrate.

Synthetic absorbable polyesters containing glycolate ester linkages are suitable substrates. Similar copolymers prepared using dioxanone instead of glycolide can also be employed, as can poly(amino acids).

Catgut, siliconized catgut, and chromic catgut can be suitable for use as substrates in certain embodiments. However, synthetic materials are generally preferred over natural materials due to their generally predictable performance and reduced inflammatory reaction.

Hemostatic Agent

In certain embodiments, it can be desirable to add an auxiliary hemostatic agent to the chitosan fiber hemostatic agents of preferred embodiments. Any suitable hemostatic agent can be deposited upon the substrates of preferred embodiments. However, in a particularly preferred embodiment, the hemostatic agent comprises bioabsorbable microporous polysaccharide microspheres (for example, TRAUMADEX™ marketed by Emergency Medical Products, Inc. of Waukesha, Wis.). The microspheres have micro-replicated porous channels. The pore size of the spheres enables water absorption and hyperconcentration of albumin, coagulation factors, and other protein and cellular components of the blood. The microspheres also impact platelet function and enhance fibrin formulation. In addition, the microspheres appear to accelerate the coagulation enzymatic reaction rate. When applied directly, with pressure, to an actively bleeding wound, the particles act as molecular sieves to extract fluids from the blood. The controlled porosity of the particle excludes platelets, red blood cells, and serum proteins larger than 25,000 Daltons, which are then concentrated on the surface of the particles. This molecular exclusion property creates a high concentration of platelets, thrombin, fibrinogen, and other proteins on the particle surface, producing a gelling action. The gelled, compacted cells and constituents accelerate the normal clotting cascade. The fibrin network formed within this dense protein-cell matrix adheres tightly to the surrounding tissue. The gelling process initiates within seconds, and the resulting clot, while exceptionally tenacious, breaks down normally along with the microparticles.

Other suitable hemostatic agents that can be employed in preferred embodiments include, but are not limited to, clotting factor concentrates, recombinant Factor VIIa (NO-VOSEVEN®); alphanate FVIII concentrate; bioclate FVIII concentrate; monoclate-P FVIII concentrate; haemate P FVIII; von Willebrand factor concentrate; helixate FVIII concentrate; hemophil-M FVIII concentrate; humate-P FVIII concentrate; hyate-C® Porcine FVIII concentrate; koate HP FVIII concentrate; kogenate FVIII concentrate; recombinate FVIII concentrate; mononine FIX concentrate; and fibrogammin P FXIII concentrate. Such hemostatic agents can be applied to the substrate in any suitable form (powder, liquid, in pure form, in a suitable excipient, on a suitable support, or the like).

A single hemostatic agent or combination of hemostatic agents can be employed. Preferred loading levels for the hemostatic agent on the substrate can vary, depending upon the nature of the substrate and hemostatic agent, the form of the substrate, and the nature of the wound to be treated. However, in general it is desirable to maximize the amount of auxiliary hemostatic agent in relation to the substrate. For example, in the case of a hemostatic puff, a weight ratio of hemostatic agent to substrate of from about 0.001:1 or lower, 0.01:1, 0.05:1, 0.1:1, 0.2:1, 0.3:1, 0.4:1, 0.5:1, 0.6:1, 0.7:1, 0.8:1, or 0.9:1 to about 1:1, 1.1:1, 1.2:1, 1.3:1, 1.4:1, 1.5:1, 1.6:1, 1.7:1, 1.8:1, 1.9:1, 2:1 or higher is generally preferred, although higher or lower ratios can be preferred for certain embodiments.

Hemostatic Materials Comprising Chitosan Support

It is generally preferred to deposit an auxiliary hemostatic agent (e.g., microporous polysaccharide microspheres) onto a hemostatic support (e.g., chitosan fibers) to yield a hemostatic material to be applied to a bleeding or oozing wound. However, in certain embodiments, chitosan fiber can be employed as an effective hemostatic material without the addition of another hemostatic agent. For example, a chitosan puff, as described below but without added microporous polysaccharide microspheres, is a particularly effective hemostatic material when applied to bleeding or oozing wounds. The various forms of chitosan (fabric, sponge, suture, fiber, and the like) as described herein, are also effective hemostatic materials in certain embodiments when employed without auxiliary agents. The preferred form of the hemostatic support can depend upon the application for which it is to be employed.

Hemostatic Puff

Hemostatic puffs or fleece are a particularly preferred form, wherein the substrate comprises a puff—a fibrous, cotton-like material that can be manipulated into a suitable shape or size so as to accommodate a particular wound configuration. FIG. 1 provides a scanning electron micrograph image of a chitosan fleece. In a preferred embodiment, a puff is prepared from chitosan fibers as follows. Chitosan fibers prepared according to conventional methods were torn or cut (manually or by mechanical apparatus) into pieces and the pieces were flattened and layered together. An acetic acid solution, glacial acetic acid, or other acidic solution (preferably a solution of a pH from 3.0-4.5) is sprayed onto a first layer to secure the chitosan fibers to each other, thereby forming a net structure. Misting chitosan fleece or fibers with glacial acetic acid results in formation of the water soluble ammonium salt of chitosan. The ammonium salt form of chitosan exhibits enhanced bioadhesion to wet tissues and increased hemostatic effect when compared to untreated chitosan fleece or fibers. Acetic acid of a desired concentration misted onto chitosan fleece or fiber can act as a "glue" to adhere the fibers together, to adhere microporous polysaccharide microspheres to the fibers, or to better adhere the chitosan fleece to wet tissues such as blood or body fluid.

Optionally, auxiliary agents in powder form, e.g., microporous polysaccharide microspheres, can be sprayed onto the first chitosan fiber layer, and then another layer of chitosan fiber is placed on top. The deposition process (acidic solution followed by deposition of another chitosan fiber layer) is then repeated and the layers built up to a desired level. Agent in powder form can be added to the fiber layers in a quantity sufficient to yield a puff comprising up to about 50, 60, 70, 80, or 90% by weight or more of the auxiliary agent. Optimal loading level, if an auxiliary agent in powder form is added, can depend upon the application and the type of auxiliary agent employed. It is generally preferred not to add auxiliary agent or other powder substances to the top layer, but in certain embodiments it can be desirable to do so. A preferred thickness for the fabric can be obtained by selecting the total number of layers.

The resulting hemostatic material is dried in an oven under vacuum to yield a hemostatic puff. While it is generally preferred to employ glacial acetic acid or an acetic acid aqueous solution, other acidic solutions of similar pH or similar characteristics can also be employed. For example, lactic acid, citric acid, glycolic acid, and mixtures of weak acids can be suitably employed. Likewise, any biologically compatible liquid that is a solvent for chitosan can also be employed, e.g., pure water, ethanolic solution, and the like. Such solutions can be acidic, basic, or neutral. In certain embodiments, it can be preferred to employ a solution that is not acidic. In such embodiments, another material in suitable form that provides adhesion between chitosan fibers can be employed, for example, gelatin, starch, carageenan, guar gum, collagen, pectin, and the like. While chitosan is a preferred substrate for preparing a hemostatic puff, other fibrous substrates, particularly fibrous polysaccharide substrates, are also suitable for use.

By adjusting the moisture level in the chitosan fibers, adhesion between the fibers and the loading capacity of any optional auxiliary agent can be optimized. The liquid in the fibers assists in adhering the fibers to each other and to compatible auxiliary agents. It can also be possible to increase the loading capacity by employing thinner fibers. The fibers can be of uniform thickness, or comprise a mixture of thicknesses. Thinner fibers can also adhere more firmly to an artery, vein, or other wound.

In preparing a hemostatic puff comprising microporous polysaccharide microsphere loaded chitosan fibers, it is generally preferred that the resulting puff contain from about 0.1 to about 95 wt. % microporous polysaccharide microspheres, more preferably from about 1 to about 60, 65, 70, 75, 80, 85, 90, or 95 wt. % microporous polysaccharide microspheres, and most preferably from about 5, 10, 15, 20, or 25 wt. % to about 30, 35, 40, 45, 50, or 55 wt. microporous polysaccharide microspheres. In certain embodiments, however, higher or lower levels of microporous polysaccharide microspheres can be preferred. If a different hemostatic agent is employed, or other components are to be added to the chitosan fibers or other substrate, different loading levels can be preferred.

To prepare a hemostatic chitosan puff that exhibits improved expandability, polyvinylalcohol (PVA) can be added to the acidic solution. An acetic acid solution containing 2 wt. % PVA yields a hemostatic puff with enhanced elasticity, but also a puff that is less hydrophilic. A high degree of hydrophilicity is generally preferred to ensure that hemostatic puff adheres securely the wound. However, in certain embodiments the reduction in hydrophilicity can be relatively small and thus not significantly affect the ability of the puff to adhere to the wound.

Hemostatic Fabric

Hemostatic fabric can be prepared from chitosan fibers according to the method described above for preparation of hemostatic puffs, with the following modifications. One or more layers of chitosan fiber, optionally loaded with an auxiliary agent, are pressed flat and dried under vacuum. It is generally preferred to use 2, 3, 4, 5, 6, 7, 8, 9, or 10 or more layers of chitosan fiber in preparing the fabric. It is generally preferred that one side of the fabric has a smooth surface and the other side of the fabric have a rough surface (e.g., in the case of chitosan, a TEFLON™ surface applied to a surface of the fiber layers during heating yields a smooth side, while a release paper applied to a surface of the fiber layers yields a rough surface). However, in certain embodiments, a fabric having two rough sides can be preferred, such as, for example, for use in connection with an irregular wound, or a deep wound, such as a lethal groin injury. In preferred embodiments, the rough surface is exposed to the wound so as to maximize contact of the chitosan fibers with the wound, resulting in an improved hemostatic effect and superior adherence to the wound. In preparing a hemostatic fabric comprising chitosan fibers loaded with microporous polysaccharide microspheres, it is generally preferred that the resulting fabric contain from about 0.01 to about 75 wt. % microporous polysaccharide microspheres, more preferably from about 1 to about 60 wt. % microporous polysaccharide microspheres, and most preferably from about 5, 10, 15, 20, or 25 wt. % to about 30, 35, 40, 45, 50, or 55 wt. % microporous polysaccharide microspheres. In certain embodiments, however, higher or lower levels of microporous polysaccharide microspheres can be preferred, or even no microspheres at all. If a different hemostatic agent is employed, or other components are to be added to the chitosan fibers or other substrate, different loading levels can be preferred.

The hemostatic fabric can be provided in the form of a sheet of a pre-selected size. Alternatively, a larger sheet of hemostatic fabric can be cut, trimmed, or folded to provide a size and shape appropriate to the wound. Although the hemostatic fabric is bioabsorbable, in cutaneous or topical applications it can be removed from the wound after a satisfactory degree of hemostasis is achieved, or it can be left in place until the wound is healed. Hemostatic fabric can be useful as artificial skin, and/or can provide antibiotic properties. When the hemostatic fabric is employed in internal applications, it is preferably left in place to be absorbed by the body over time. Such hemostatic fabrics are particularly well suited for use in the treatment of oozing wounds, such as in tumor beds or brain tissue.

Hemostatic Sponge

A hemostatic sponge can be prepared according to methods known in the art for preparing a porous sponge from a biocompatible or bioabsorbable polymeric material, e.g., chitosan. Such methods typically involve preparation of a solution of the polymeric material, crosslinking agents, and foaming agents. The sponge can be loaded with hemostatic agent at any convenient point or points in the process, e.g., during formation of the sponge, or after preparation of the sponge.

Hemostatic Sutures

The hemostatic substrates of preferred embodiments can be fabricated into sutures. In a preferred embodiment, chitosan fibers are fabricated into microsutures. Processes for suture fabrication include extrusion, melt spinning, braiding, and many other such processes. The synthesis of raw suture materials is accomplished by any number of processes known within the textile industry. Suture sizes are given by a number representing diameter ranging in descending order from 10 to 1 and then 1-0 to 12-0, with 10 being the largest and 12-0 being the smallest. Sutures can comprise monofilaments or many filaments twisted together, spun together, or braided. The sutures of preferred embodiments exhibit satisfactory properties, including stress-strain relationship, tensile strength, rate of retention, flexibility, intrinsic viscosity, wettability, surface morphology, degradation, thermal properties, contact angle of knots, and elasticity. Hemostatic sutures can be employed in any suitable application. However, they are generally not preferred for vessel anastamosis, since their hemostatic properties can result in undesired clot formation within the vessel.

Hemostatic Powders

The hemostatic substrates of preferred embodiments can be formed into a powder and applied in such form directly to a wound. For example, chitosan particles, optionally combined with other materials, can be employed as a void filler following tooth extraction.

Hemostatic Matrices

Three-dimensional porous matrices can be prepared from sintered polymer particles, for example, chitosan particles, and medicaments or therapeutic agents can be infused into the pores. Alternatively, microcapsules comprising a chitosan shell encapsulating a medicament or therapeutic agent can be sintered to form a matrix.

Wound Dressings

While it is generally preferred to apply the hemostatic material (for example, a hemostatic fabric, sponge, puff, or powder prepared as described above) directly to the wound, and while the hemostatic material exhibits satisfactory adhesion to many types of wounds, in certain embodiments it can be preferred to incorporate the hemostatic material into a wound dressing including other components.

To ensure that the hemostatic material remains affixed to the wound, a suitable adhesive can be employed, for example, along the edges of one side of the hemostatic fabric, sponge or puff. Although any adhesive suitable for forming a bond with skin can be used, it is generally preferred to use a pressure sensitive adhesive. Pressure sensitive adhesives are generally defined as adhesives that adhere to a substrate when a light pressure is applied but leave no residue when removed. Pressure sensitive adhesives include, but are not limited to, solvent in solution adhesives, hot melt adhesives, aqueous emulsion adhesives, calenderable adhesive, and radiation curable adhesives. Solution adhesives are preferred for most uses because of their ease of application and versatility. Hot melt adhesives are typically based on resin-tackified block copolymers. Aqueous emulsion adhesives include those prepared using acrylic copolymers, butadiene styrene copolymers, and natural rubber latex. Radiation curable adhesives typically consist of acrylic oligomers and monomers, which cure to form a pressure sensitive adhesive upon exposure to ultraviolet lights.

The most commonly used elastomers in pressure sensitive adhesives include natural rubbers, styrene-butadiene latexes, polyisobutylene, butyl rubbers, acrylics, and silicones. In preferred embodiments, acrylic polymer or silicone based pressure sensitive adhesives are used. Acrylic polymers generally have a low level of allergenicity, are cleanly removable from skin, possess a low odor, and exhibit low rates of mechanical and chemical irritation. Medical grade silicone pressure sensitive adhesives are preferred for their biocompatibility.

Amongst the factors that influence the suitability for a pressure sensitive adhesive for use in wound dressings of preferred embodiments are the absence of skin irritating components, sufficient cohesive strength such that the adhesive can be cleanly removed from the skin, ability to accommodate skin movement without excessive mechanical skin irritation, and good resistance to body fluids.

In preferred embodiments, the pressure sensitive adhesive comprises a butyl acrylate. While butyl acrylate pressure sensitive adhesives are generally preferred for many applications, any pressure sensitive adhesive suitable for bonding skin can be used. Such pressure sensitive adhesives are well known in the art.

As discussed above, the hemostatic materials of preferred embodiments generally exhibit good adherence to wounds such that an adhesive, for example, a pressure sensitive adhesive, is not necessary. However, for ease of use and to ensure that the hemostatic material remains in a fixed position after application to the wound, it can be preferable to employ a pressure sensitive adhesive.

While the hemostatic fabrics and other hemostatic materials of preferred embodiments generally exhibit good mechanical strength and wound protection, in certain embodiments it can be preferred to employ a backing or other material on one side of the hemostatic material. For example, a composite including two or more layers can be prepared, wherein one of the layers is the hemostatic material and another layer is, e.g., an elastomeric layer, gauze, vapor-permeable film, waterproof film, a woven or nonwoven fabric, a mesh, or the like. The layers can then be bonded using any suitable method, e.g., adhesives such as pressure sensitive adhesives, hot melt adhesives, curable adhesives, application of heat or pressure such as in lamination, physical attachment through the use of stitching, studs, other fasteners, or the like.

Interaction between Chitosan Fibers and Wound

Chitosan fibers of preferred embodiments exhibits a hemostatic effect when placed in a bleeding or oozing wound. The physical and chemical characteristics chitosan fiber were examined to determine the mechanism of their hemostatic action and to maximize their hemostatic effect. While not wishing to be bound to any particular theory, and while the mechanism of chitosan's hemostatic function has not yet been definitively elucidated, it is believed that its calcium content plays a significant role in hemostasis. The calcium can stimulate platelets to release b-TG, PF-4 factors, or other substances involved in the hemostasis process.

The content of calcium in a 0.2 g sample of chitosan (prepared by deacetylation, 91.8 wt. % purity, 1000 kD molecular weight) was measured at 0.238 wt. %. Calcium content was measured by Inductively Coupled Plasma (ICP) quantometer measurements performed with a Jarrell-Ash-1100 ICP-Auger Electron Spectroscopy (AES) instrument at a pressure of 1.6-105 Pa, under an argon atmosphere. Sample preparation involved, as a first step, dissolving the chitosan fiber in concentrated nitric acid. The solution was allowed to stand for two hours, after which it was boiled until all of the water in solution was vaporized. The residue remaining was dissolved in a 100 ml volume of 1 M nitric acid, and calcium content was then determined.

The literature suggests that the hemostatic effect of chitosan may not follow the coagulation cascade pathways as described above, because chitosan can still cause coagulation of blood from which all of the platelets, white blood cells, and plasma have been removed. Chitosan's hemostatic effect is most likely due to its ability to cause erythrocytes to coalesce to each other, thereby forming a blood clot. When chitosan fibers come into contact with blood, the blood penetrates into the network formed by chitosan fibers. Chitosan is hydrophilic and is wettable to form a hydrogel. The porous hydrogel can either absorb blood cells or provide enough space for the blood cells to diffuse into it. These factors can induce hemostasis by causing erythrocytes to coalesce and to form a blood clot. Another hypothesis is that chitosan, a naturally positively charged polysaccharide, can interact with negative charges on the surface of blood proteins to cause erythrocytes to coalesce to each other.

Chitosan is hydrophilic and biodegradable, and exhibits biocompatibility hemostatic properties. It is easily and effectively combined with other materials, such as microporous polysaccharide microspheres, and exhibits strong physical adsorption and adhesion amongst fibers. Chitosan also bonds strongly to microporous polysaccharide microspheres, possibly due to the similarity in their skeletal chemical structures, both of which are based on glucose units. Chitosan has a strong affinity to cells, thereby resulting in an effective hemostatic material.

The loading efficiency of microporous polysaccharide microspheres in a puff comprising chitosan fibers was determined. Loading efficiencies of up to 90% can be achieved while maintaining the pliability of the puff. At loading efficiencies above 90%, hardening of the puff can result, but can be acceptable in certain embodiments.

When chitosan fibers are loaded or combined with another polysaccharide material, such as microporous polysaccharide microspheres, various adhering or bonding mechanisms can be involved. In one mechanism, electrostatic forces maintain contact between the fibers, between the microporous polysaccharide microspheres, or between the microporous polysaccharide microspheres and the chitosan fibers. In another mechanism, the particles are held in place by physical forces, with the chitosan fiber forms a lattice or matrix that supports the microporous polysaccharide microspheres. In yet another mechanism, an acidic solution added to the chitosan fibers and the microporous polysaccharide microspheres causes components to solubilize and bond together.

While chitosan fibers can be bonded or adhered each other (or to microporous polysaccharide microspheres) by any of the three methods referred to above (electrostatic forces, physically, or chemically), it is generally preferred to employ a combination of two or more different mechanisms, so as to produce optimal loading of the fleece, for example, static and physical, static and chemical, physical and chemical, or static and physical and chemical.

The expansion of microporous polysaccharide microspheres and chitosan after they contact water was measured. It was observed that pure microporous polysaccharide microspheres absorb water and expand to generate pressure against surrounding structures. However, there was no clinically significant expansion of microporous polysaccharide microspheres deposited on a chitosan fiber puff upon contact with water. The measurements were conducted as follows: 19 g of TRAUMADEX™ microporous polysaccharide microspheres were placed in a device, the diameter of which was 1.55 cm, to measure expansion. Water was added to the TRAUMADEX™, resulting in the water's adsorption. Weight was added to the top of the device to prevent TRAUMADEX™ from expanding. The weight added corresponds to the pressure that TRAUMADEX™ produces after it contacts water. In the experiment, the difference in the weight applied before contact of the TRAUMADEX™ with water and the weight applied after contact of the TRAUMADEX™ with water was 270 g. Accordingly, the pressure which TRAUMADEX™ exerted after it contacted water was 107 mm Hg. The same method was employed to measure the expansion of TRAUMADEX™ deposited on a chitosan puff, but the volume change observed was too small to be measured. It is believed that the porous chitosan puff provides sufficient space for the expanded TRAUMADEX™ such that no significant volume change of the TRAUMADEX™ deposited on the chitosan puff can be detected upon contact with water.

Closure of Femoral Artery Puncture Wounds

Figure 2:
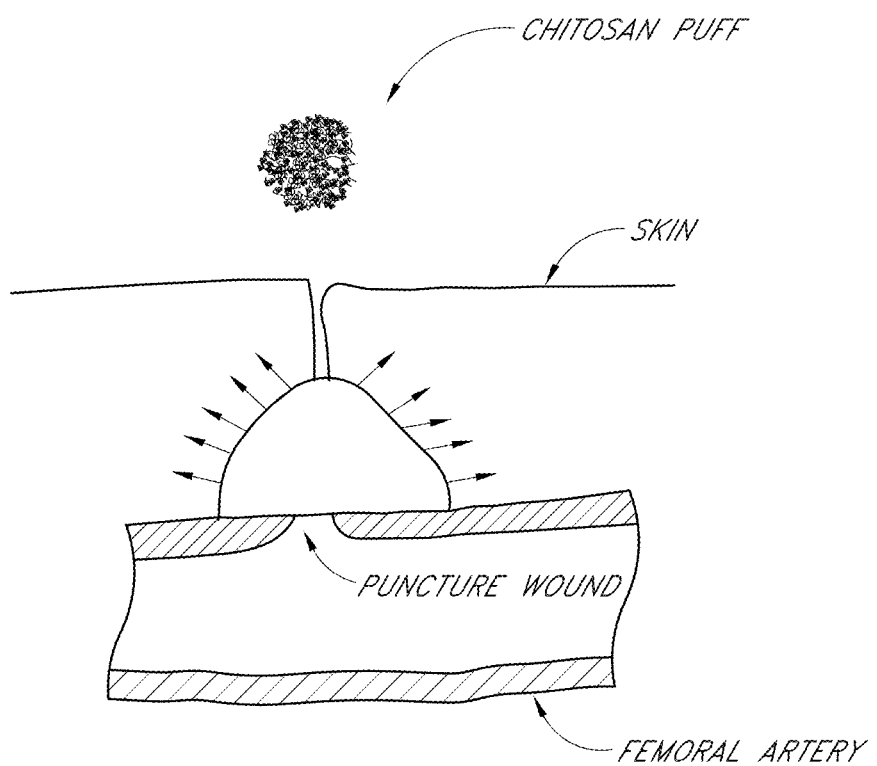
FIG. 2 depicts sealing a femoral artery puncture with a hemostatic puff. The expandable, absorbable, biologically-compatible chitosan puff is placed against the puncture wound via an incision in the skin. The hemostatic sponge expands and holds itself in place against the wall of the artery, sealing the puncture.
Figure 3:
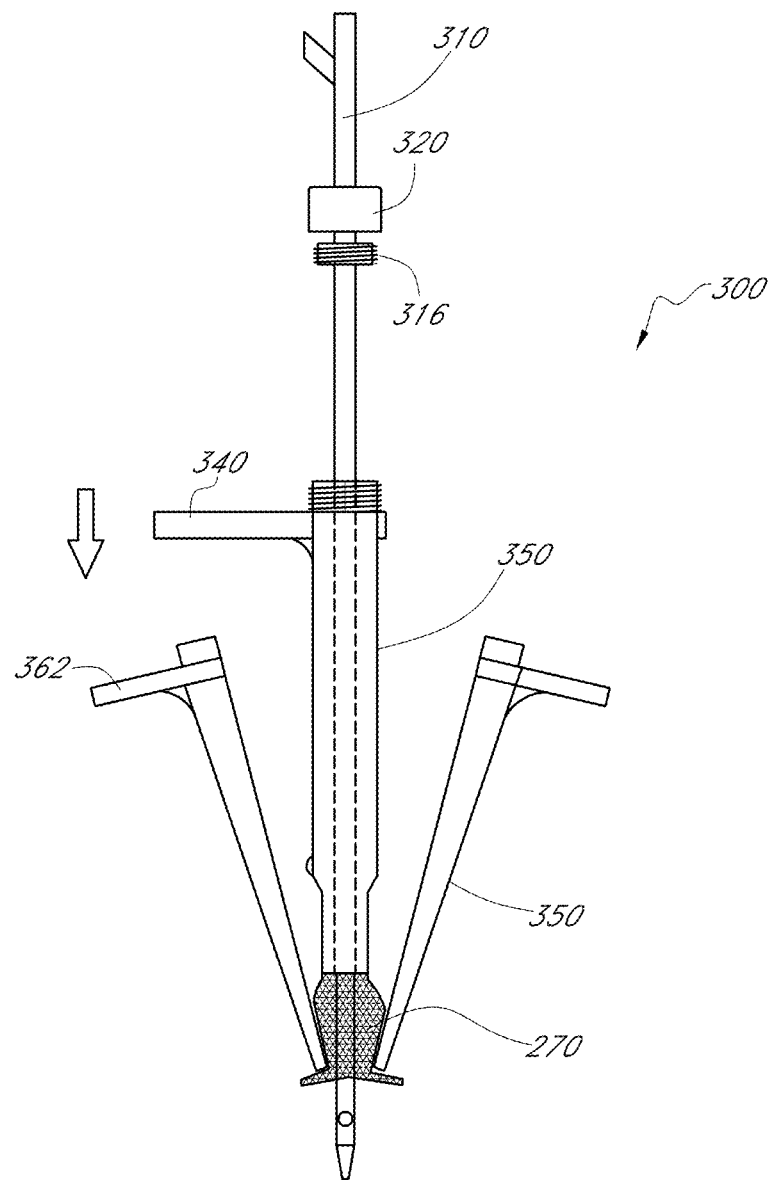
FIG. 3 depicts a device for sealing an artery puncture with a hemostatic fleece.

A hemostatic puff was developed for use in conjunction with a femoral artery puncture wound closure device, described in copending U.S. patent application Ser. No. 10/463,754, filed Jun. 16, 2003, and entitled "VASCULAR WOUND CLOSURE DEVICE AND METHOD", the contents of which is hereby incorporated by reference in its entirety. FIG. 2 depicts sealing a femoral artery puncture with a hemostatic puff. The hemostatic puff can be wrapped around the blood indication catheter of the wound closure device, depicted in FIG. 3, so as to be efficiently and effectively delivered to the top of the puncture wound. The vascular wound closure device 300 depicted in FIG. 3 comprises a catheter 310 having a proximal end and a distal end defining a lumen therebetween, and can be used for placing a hemostatic puff 270 to the top of a puncture wound. A coupling member 320 is movably disposed about the catheter 310 and is configured to mechanically couple to the stop member 316. The device has a handle 340 and handle 362 and a delivery tube 350. In a particularly preferred embodiment, the hemostatic puff, optionally with an adhesive or other substance providing enhanced adhesion to the wound, are delivered to the wound by the wound closure device.

In a venous laceration, the conventional method of repairing the laceration involves temporarily stopping the bleeding, occluding the vein, suctioning out the blood, then suturing or clipping the laceration to repair it. A vessel patch can also be required in conventional methods. The hemostatic fabrics of preferred embodiments can also be employed to treat venous or arterial lacerations merely by compressing the fabric to the laceration and allowing it to remain in place and eventually be absorbed by the body.

Closure of Wounds Using Endoscopic Devices

The chitosan fleece of preferred embodiments is particularly suitable for use in connection with endoscopic or luminal devices, especially endoscopic devices for use in gastrointestinal applications, for controlling bleeding. Chitosan fleece can be manipulated into a small puff, which can be inserted through the lumen of the endoscope to be placed on a wound, or to treat bleeding. For example, a 2 mm diameter puff of chitosan fleece, or a puff of another size suitable to the inner diameter of the lumen of the device, can be inserted through the endoscope and used to control gastrointestinal or other bleeding, e.g., bleeding from ulcers, tumors, or lesions, or bleeding resulting from surgical procedures such as tumor removal.

Preparation of Chitosan

Chitin is present in crustacean shells as a composite with proteins and calcium salts. Chitin is produced by removing calcium carbonate and protein from these shells, and chitosan is produced by deacetylation of chitin in a strong alkali solution. U.S. Pat. No. 3,533,940, the contents of which are incorporated by reference herein in its entirety, describes a method for the preparation of chitosan.

A preferred method for obtaining chitosan from crab or other crustacean shells is as follows. Calcium carbonate is removed by immersing the shell in dilute hydrochloric acid at room temperature for 24 hours (demineralization). Proteins are then extracted from the decalcified shells by boiling them with dilute aqueous sodium hydroxide for six hours (deproteinization). The demineralization and deproteinization steps are preferably repeated at least two times to remove substantially all of the inorganic materials and proteins from the crustacean shells. The crude chitin thus obtained is washed then dried. The chitin is heated at 140° C. in a strong alkali solution (50 wt. %) for 3 hours. Highly deacetylated chitosan exhibiting no significant degradation of molecular chain is then obtained by intermittently washing the intermediate product in water two or more times during the alkali treatment.

Figure 4:
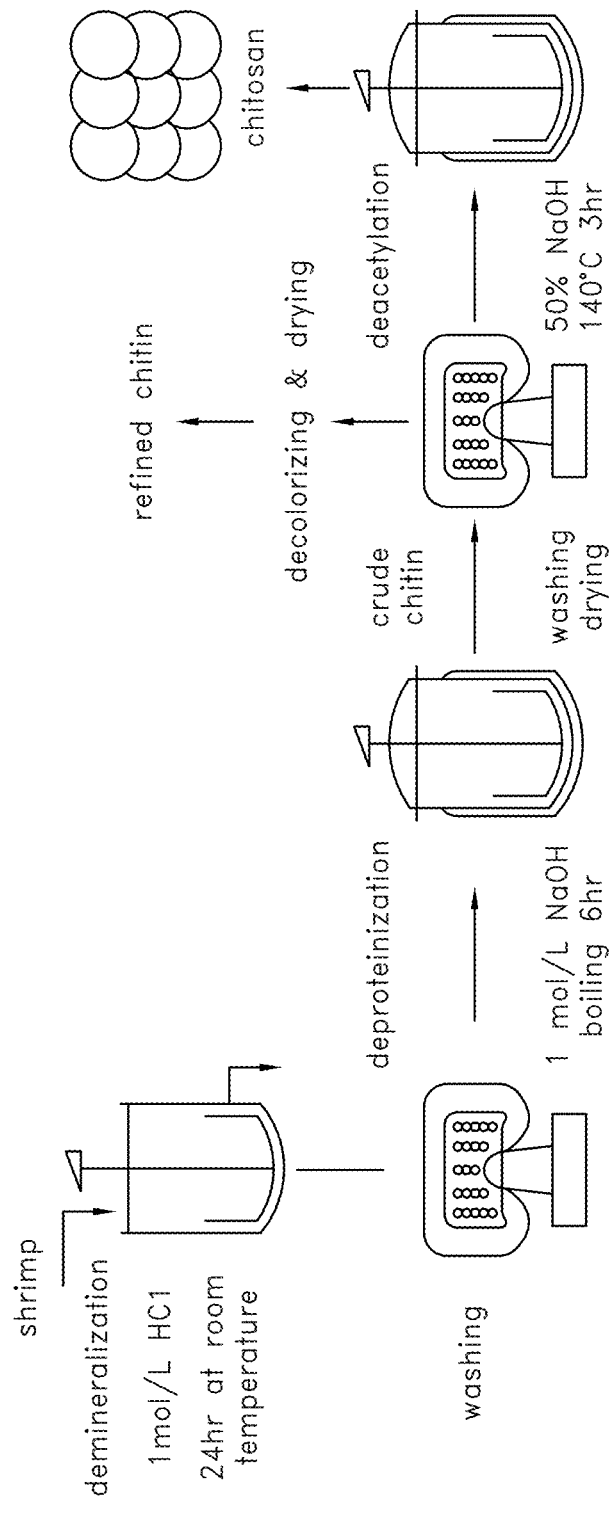
FIG. 4 schematically depicts a process for obtaining chitosan from shrimp waste.

A process for obtaining chitosan from shrimp waste is schematically depicted in FIG. 4.

Preparation of Chitosan Fiber

Figure 5:
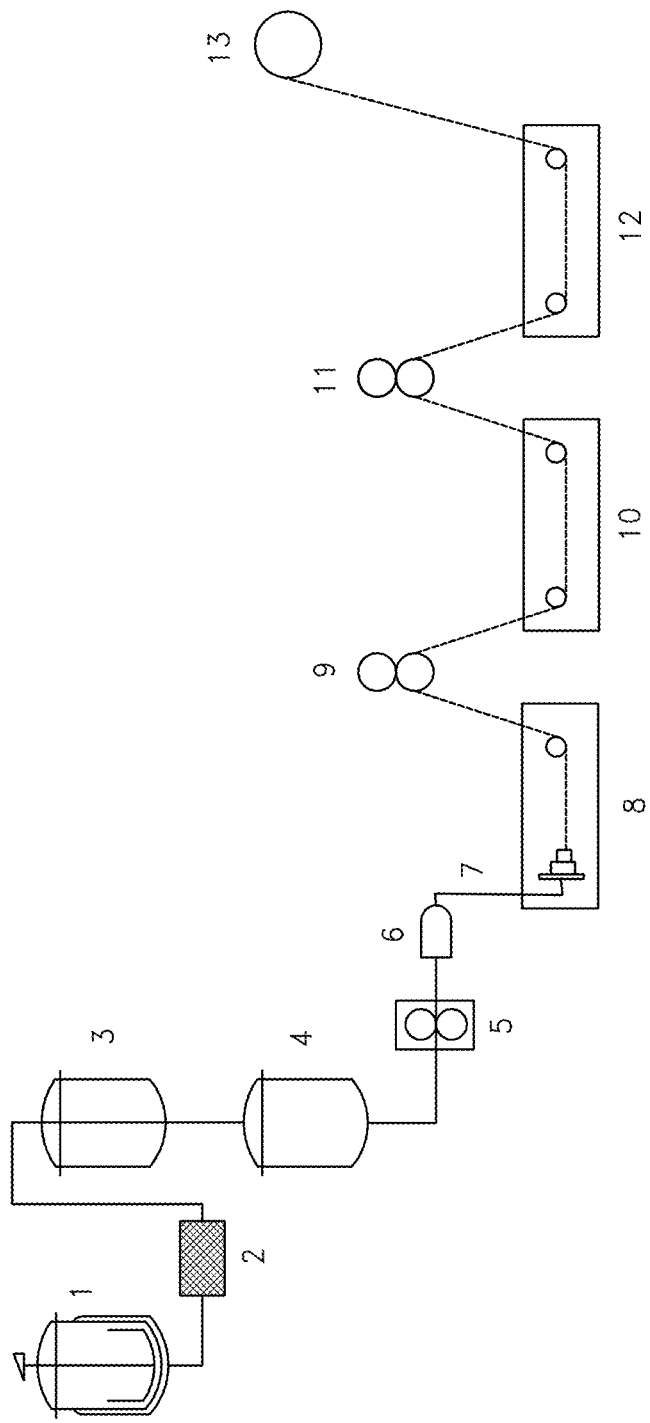
FIG. 5 schematically depicts an apparatus for preparing chitosan fibers.

In a preferred embodiment, a wet spinning method is employed to prepare chitosan fiber. First, chitosan is dissolved in a suitable solvent to yield a primary spinning solution. Preferred solvents include acidic solutions, for example, solutions containing trichloroacetic acetic acid, acetic acid, lactic acid, and the like, however any suitable solvent can be employed. The primary spinning solution is filtered and deaerated, after which it is sprayed under pressure into a solidifying bath through the pores of a spinning jet. Solid chitosan fibers are recovered from the solidified bath. The fibers can be subjected to further processing steps, including but not limited to drawing, washing, drying, post treatment, functionalization, and the like. FIG. 5 schematically depicts an apparatus for preparing chitosan fibers. The apparatus includes a dissolving kettle 1, a filter 2, a middle tank 3, a storage tank 4, a dosage pump 5, a filter 6, a spinning jet 7, a solidifying bath 8, a pickup roll 9, a draw bath 10, a draw roll 11, a washing bath 12, and a coiling roll 13.

A preferred method for preparing chitosan fiber suitable for fabrication into the hemostatic materials of preferred embodiments is as follows. The primary chitosan spinning solution is prepared by dissolving 3 parts chitosan powder in a mixed solvent at 5° C. containing 50 parts trichloroacetic acid (TDA) to 50 parts methylene dichloride. The resulting primary spinning solution is filtered and then deaerated under vacuum. A first solidifying bath comprising acetone at 14° C. is employed. The aperture of the spinning jet is 0.08 mm, the hole count is forty-eight, and the spinning velocity is 10 m/min. The spinning solution is maintained at 20° C. by heating with recycled hot water. The chitosan fibers from the acetone bath are recovered and conveyed via a conveyor belt to a second solidifying bath comprising methanol at 15° C. The fibers are maintained in the second solidifying bath for ten minutes. The fibers are recovered and then coiled at a velocity of 9 m/min. The coiled fibers are neutralized in a 0.3 g/l KOH solution for one hour, and are then washed with deionized water. The resulting chitosan fiber is then dried, after which it is ready for fabrication into the hemostatic materials of preferred embodiments.

In a particularly preferred embodiment, glacial, or anhydrous, acetic acid is employed as an agent to adhere the chitosan fibers to each other in embodiments where chitosan fibers, either alone or with an added medicament, therapeutic agent or other agent, are used in forming a hemostatic agent. In addition to providing good adherence between the chitosan fibers, fibers treated with glacial acetic acid also exhibit exceptional ability to adhere to wounds, including arterial or femoral wounds.

Depending upon the application, the concentration of acetic acid in solution can be adjusted to provide the desired degree of adhesion. For example, it can be desirable to employ a reduced concentration of acetic acid if the chitosan fibers are to be employed in treating a seeping wound or other wound where strong adhesion is not desired, or in applications where the hemostatic agent is to be removed from the wound. In such embodiments, an acetic concentration of from about 1 vol. % or less to about 20 vol. % is generally employed, and more preferably a concentration of from about 2, 3, 4, 5, 6, 7, 8, 9, or 10 vol. % to about 11, 12, 13, 14, 15, 16, 17, 18, or 19 vol. % is employed. Where strong adhesion between fibers, or strong adhesion to the wound is desired, a concentration greater than or equal to about 20 vol. % is preferred, more a preferably from about 50, 55, 60, 65, or 70 vol. % to about 75, 80, 85, 90, 95, or 100 vol. %, and most preferably from about 95, 96, 97, 98, or 99 vol. % to about 100 vol. %.

Experiments

Preparation of Chitosan Fleece

Figure 6:
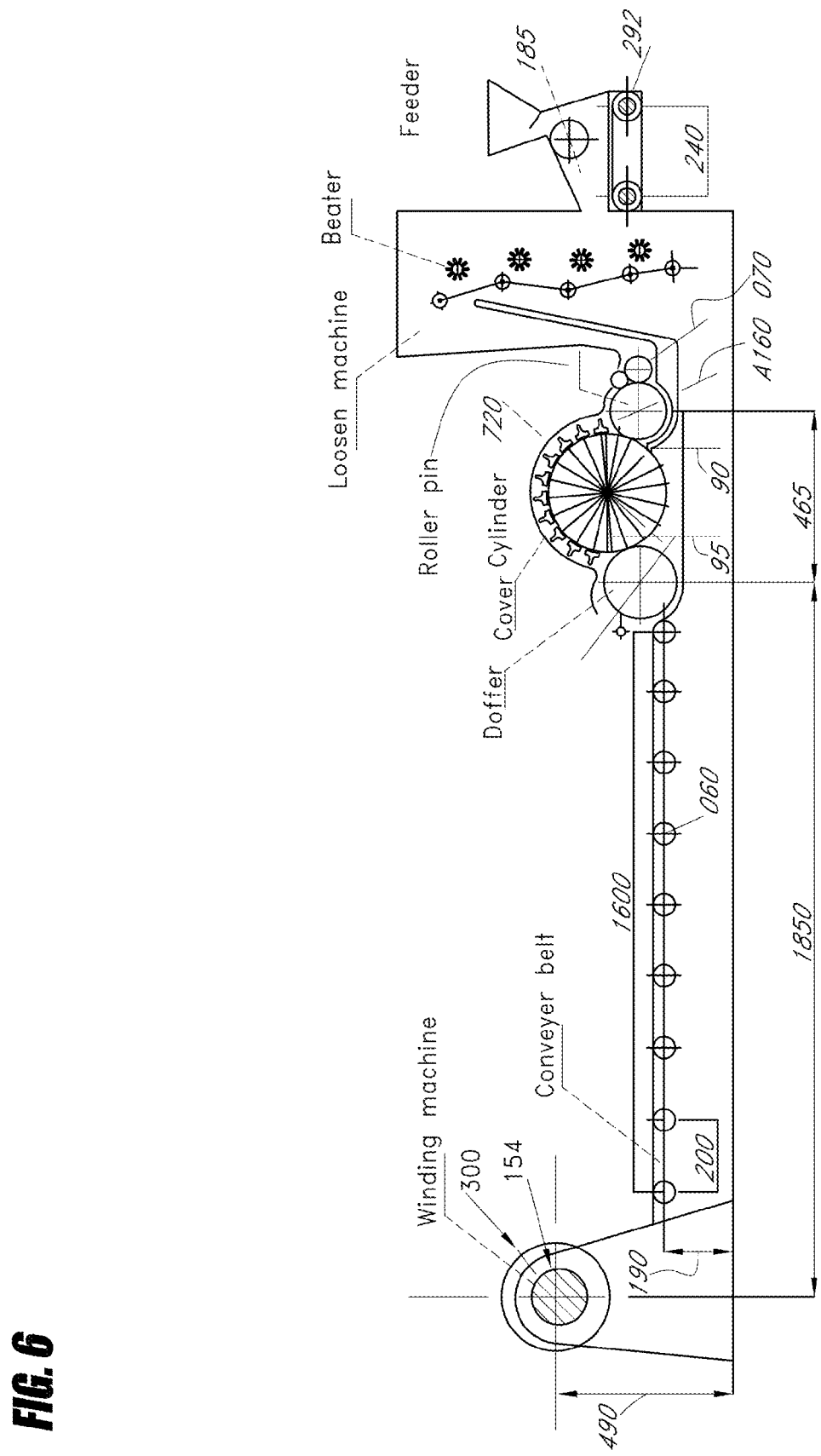
FIG. 6 provides a schematic of an assembly line for production of chitosan fleece, including a feeder, loosen machine, carding machine, conveyer belt and winding machine.

Chitosan fleece can be prepared using equipment commonly employed in the textile industry for fiber production. A typical assembly line for production of chitosan fleece can employ a feeder, a loosen machine, a carding machine, a conveyor belt, and lastly a winding machine, as depicted in FIG. 6. In the feeder, chitosan short fiber is fed through a feeder and into a loosen machine, wherein chitosan short fiber is loosened by several beaters. In the carding machine, chitosan fibers are ripped and turned into chitosan fleece by high speed spinning of a cylinder and roller pin, then the fleece is peeled off as a separated thin layer of net by a duffer. A thin layer of chitosan fleece net separated from the duffer moves on the conveyer belt. A controlled aqueous solution of acetic acid is sprayed on the chitosan fleece and then a specified amount of microporous polysaccharide microspheres is distributed homogeneously while the chitosan fleece net is moving on the conveyer belt. The chitosan fleece loaded with microporous polysaccharide microspheres is then collected by a reel and then is sent to a vacuum oven for drying.

Characterization of Chitosan Fiber

Determination of the Water Content 1.0 g chitosan fabric puff ($W_1$) was accurately weighted in a clean and dried beaker, and then the beaker was removed into an oven at 100° C. for 12 hours. The dried chitosan sample was weighted again ($W_2$), and then the water content was calculated as following formula:

$$\alpha=(W_1-W_2)/W_2$$

Determination of Average Molecular Weight

Dried chitosan of 0.3 g was accurately weighted and dissolved in 0.1 mol L$^{-1}$ CH$_3$COONa-0.2 mol L$^{-1}$ CH$_3$COOH solution. Five different concentrations of chitosan solutions were prepared. The relative viscosity was measured at 25±0.5° C. in a constant temperature water bath with a Ubbelohde viscometer. Intrinsic viscosity is defined as:

$$[\eta]C(\eta_{red}) \rightarrow 0$$

and is obtained by extrapolating the reduced viscosity versus concentration data to zero concentration. See, e.g., Qurashi T, Blair H S, Allen S J, *J. Appl. Polym. Sci.*, 46:255 (1992). The intercept on the ordinate is the intrinsic viscosity. The viscosity average-molecular weight was calculated based on the Mark-Houwink equation as follows:

$$[\eta]=KM^\alpha$$

where K=1.81×10$^{-3}$ L/g, $\alpha$=0.93.

Determination of the Degree of Deacetylation

The measurements were made by the modified method reported by Broussignac, Chem. Ind. Genie. Chim. 99:1241 (1969). Dried chitosan in an amount of 0.3 g was accurately weighted and dissolved in 0.1 mol L$^{-1}$ HCl. The solution was titrated with 0.1 mol L$^{-1}$ NaOH using bromocresol green as an indicator. The degree of deacetylation was calculated as follow:

$$NH_2\% = \frac{(C_1V_1 - C_2V_2) \times 0.016}{G(100-W)} \times 100$$

wherein $C_1$ is the concentration of HCl (mol L$^{-1}$); $C_2$ is the concentration of NaOH (mol L$^{-1}$); $V_1$ is the volume of HCl (ml); $V_2$ is the volume of NaOH (ml); G is the sample weight; W is the water percentage of sample (%); and 0.016 is the weight of NH$_2$ equal to 1 ml 0.1 mol L$^{-1}$ HCl (g).

$$\text{Degree of deacetylation (\%)=NH}_2\%/9.94\% \times 100\%$$

wherein 9.94% is the theoretical NH$_2$ percentage when 100% of the CH$_3$CONH— group was deacetylated.

Determination of Heavy Metal Contents (Cr, Cu, Zn, Pb, Hg)

The Cr, Cu, Zn, and Pb contents were determined by an Inductively Coupled Plasma Atomic Emission Spectrometry (ICP-AES) method. Before measurement, the chitosan sample was treated as follows: a 0.1 g chitosan sample was accurately weighed, and then was soaked into a crucible which contained 2 mL of 90% nitric acid and 0.6 ml of 50% HClO$_4$. The chitosan sample was gradually dissolved in the mixed acid solution, and simultaneously underwent oxidative degradation. After reacting for 2 hrs, the dissolved sample was slowly heated to slowly vaporize all of the liquid, and then was combusted by a burner until all the organic components decomposed and disappeared. The residue containing inorganic salts was diluted by a 2% nitric acid solution to 10 mL and then the heavy metal contents were measured by ICP-AES (Jarrell-Ash 1100+2000 ICP-AES).

The mercury content in chitosan was determined by Atomic Absorption Spectrometry (AAS). A sample of 0.1 g accurately weighed chitosan was dissolved in 10 mL 2% nitric acid. Mercury content of this sample was then measured by AAS.

Analysis of Chitosan Sample 1 yielded the following results: water content: 11.75%; molecular weight: 1326 kDa; degree of deacetylation: 91.2%; metal content (μg/g): Al 59.1, Ba 2.95, Ca 187, Cr 8.86, Cu 3.76, Fe 34.9, Mg 59.1, Na 169, Si 185, Pb 16.3, Zn 25.5, Hg 0.16.

Analysis of Chitosan Sample 2 yielded the following results: water content: 12.38%; molecular weight: 1407 kDa; degree of deacetylation: 93.6%; metal content (μg/g): Al 106, Ba 4.36, Ca 751, Cr 12.6, Cu 40.7, Fe 116, Mg 319, Na 193, Si 973, Pb 8.76, Zn 8.47×10$^3$, Hg 0.16

The quality of the chitosan fiber tested was acceptable, based on the results of analysis of Chitosan Samples 1 and 2, each of which had an average molecular weight >1000 kDa (1 million), a degree of deacetylation >90%, and a harmful heavy metal (Cr, Cu, Pb, Hg) content that was very low (except for Zn content in Chitosan Sample 2).

Loading Percentage of Microporous Polysaccharide Microspheres and the Quality of the Chitosan Fleece Increased loading percentage of microporous polysaccharide microspheres can be achieved by utilizing two-step manufacturing processes. The first step is to loosen the chitosan fibers and the second step is to card the loosened chitosan fibers into a thin layer of chitosan fleece. The quality of chitosan fleece can directly affect the loading percentage of a hemostatic agent such as microporous polysaccharide microspheres, which in turn can affect the fleece's hemostatic function. The microporous polysaccharide microspheres loading percentage of samples can be increased from less than or equal to 25 wt. % up to 30-40% when the above-described two-step process is employed.

Preparation of Chitosan Puff

A hemostatic puff can be prepared from chitosan fibers by building up layers of chitosan fiber and microporous polysaccharide microspheres "glued" together using an acetic acid solution, which are then dried under vacuum. A "glue" solution was prepared comprising an acetic acid solution with a pH value of from 3.0 to 4.5. The chitosan fibers were torn into pieces. After laying down a first layer of chitosan pieces, the acetic acid solution was sprayed onto the chitosan pieces, and then the microporous polysaccharide microspheres were added. A second layer was formed upon the first layer by the same procedure. Layers were built up in this fashion until seven layers were obtained, except that no microporous polysaccharide microspheres were added to the topmost layer. The acetic acid solution acted not only as a glue between chitosan layers, but also increased the hemostatic powder's ability to adhere to the chitosan fibers. Alternatively, a hemostatic puff comprising only chitosan fibers can be prepared according to the method described above by omitting the steps of adding microporous polysaccharide microspheres to the chitosan layers. Loading efficiency for microporous polysaccharide microspheres in hemostatic puffs prepared as described above is provided in Table 1.

TABLE 1

Drug Loading Efficiency of Chitosan (CS) Puff

| CS weight (g) after drying/before drying | Drug (g) | CS + drug (after drying) (g) | Loading efficiency | Fiber Condition |
|---|---|---|---|---|
| 1.96/(2.19) | 0 | 1.96 | — | loose/flexible |
| 1.92/(2.15) | 0.25 | 2.15 | 92.0% | loose/flexible |

TABLE 1-continued

Drug Loading Efficiency of Chitosan (CS) Puff

| CS weight (g) after drying/before drying | Drug (g) | CS + drug (after drying) (g) | Loading efficiency | Fiber Condition |
|---|---|---|---|---|
| 1.82/(2.03) | 0.51 | 2.28 | 90.1% | loose/flexible |
| 1.98/(2.21)* | 1.01 | 2.96 | 97.0% | hard |

*Two times as much water was sprayed onto the fibers compared to that used in the other examples.

This hemostatic chitosan puffs thus prepared exhibited good hemostatic function and swelling ability. When placed on or in a wound, the puffs absorbed the blood immediately. The blood would pass through the first few chitosan layers, then immediately solidify to prevent further bleeding. Such hemostatic chitosan puffs biodegrade to nontoxic materials in the body after a period time, thus surgery is not needed to remove the puff if it is placed internally.

To improve the elasticity of the hemostatic puff, the chitosan fibers were modified with CELVOL™ 205 PVA (manufactured by Celanese Ltd. of Dallas, Tex., partially hydrolyzed polymer of acetic acid ethenyl ester with ethenol) to decrease their hydrophilicity. The procedure for preparing PVA modified hemostatic puff is similar to the procedure for preparing unmodified puff, the primary difference being that PVA is added to acetic acid solution applied to the chitosan layers. The concentration of PVA in the acetic solution was 2 wt. %. The PVA modified puff exhibited slightly improved elasticity when compared to the unmodified puff.

Preparation of Chitosan Sponge

A hemostatic sponge is prepared according to the following procedure. Chitosan and PVA are dissolved in dilute acetic acid solution. Palladium chloride is added as a catalyst and toluene diisocyanate is added as a foaming agent and cross-linking agent. The crude product is washed with ammonia solution and dried in an oven. The sponge is optionally loaded with a medicament or therapeutic agent either by adding the hemostatic agent to the acetic acid solution before preparation of the sponge, or by loading it into the sponge after it is prepared.

Preparation of Chitosan Fabric

Hemostatic fabric was prepared according to the following procedure. First, an aqueous solution of 1 wt. % acetic acid with a pH of 3.0 was prepared. Chitosan fiber was separated into pieces and homogeneously laid on a glass plate covered with releasing paper to form a thin layer. The aqueous acetic acid solution was sprayed onto the chitosan fiber surface, and a specified amount of hemostatic powder was distributed over the chitosan fiber. Additional layers were built up by the same procedure. After a small amount of aqueous acetic acid solution was sprayed onto the uppermost chitosan fiber layer, a flat plate of polytetrafluoroethylene (TEFLON™) was placed on the uppermost chitosan fiber layer. Samples comprising five layers were thus prepared.

The entire system was placed in a vacuum oven and dried under vacuum for three hours at 50° C. The TEFLON™ plate and releasing paper were removed, and the non-woven hemostatic fabric was recovered. The upper layer which was in contact with the TEFLON™ plate was covered with a thin membrane of chitosan, and the bottom layer which was in contact with the releasing paper was made up of nonwoven fibrous chitosan having a rough surface.

Figure 7:
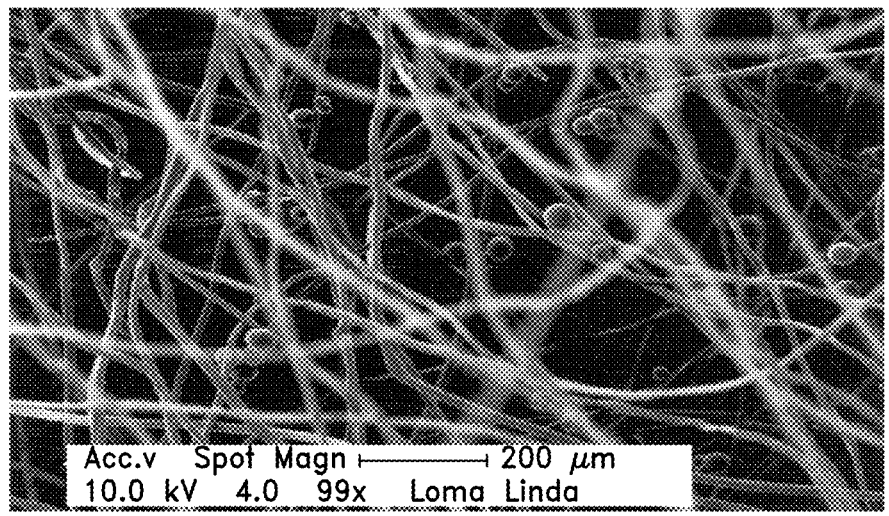
FIG. 7 provides a scanning electron micrograph of chitosan fleece loaded with 15% microporous polysaccharide microspheres.
Figure 8:
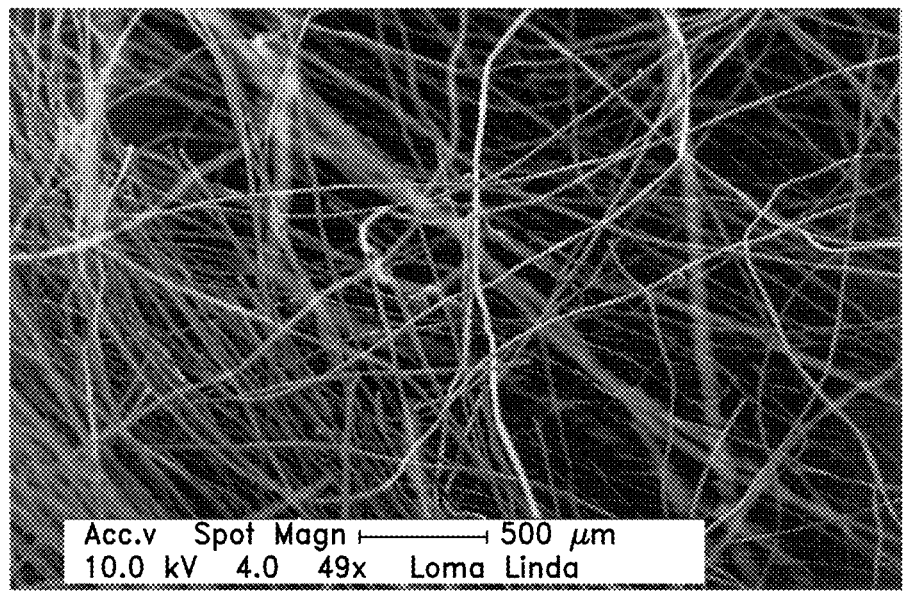
FIG. 8 provides a scanning electron micrograph of chitosan fleece loaded with 60% microporous polysaccharide microspheres.
Figure 10A:
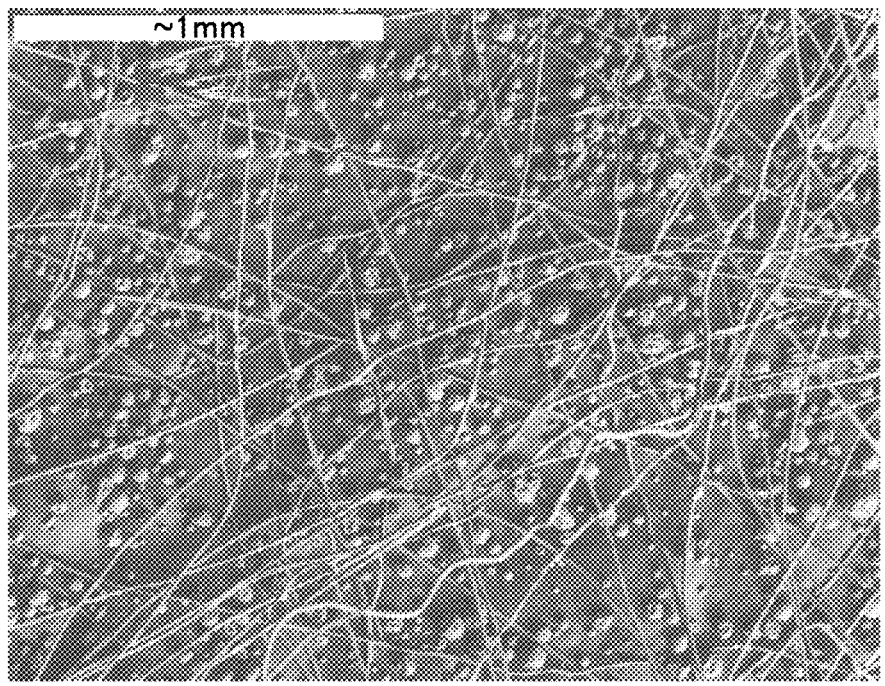
FIGS. 10A, 10B, and 10C provide SEM images of microporous polysaccharide microspheres physically loaded onto chitosan fleece.
Figure 10B:
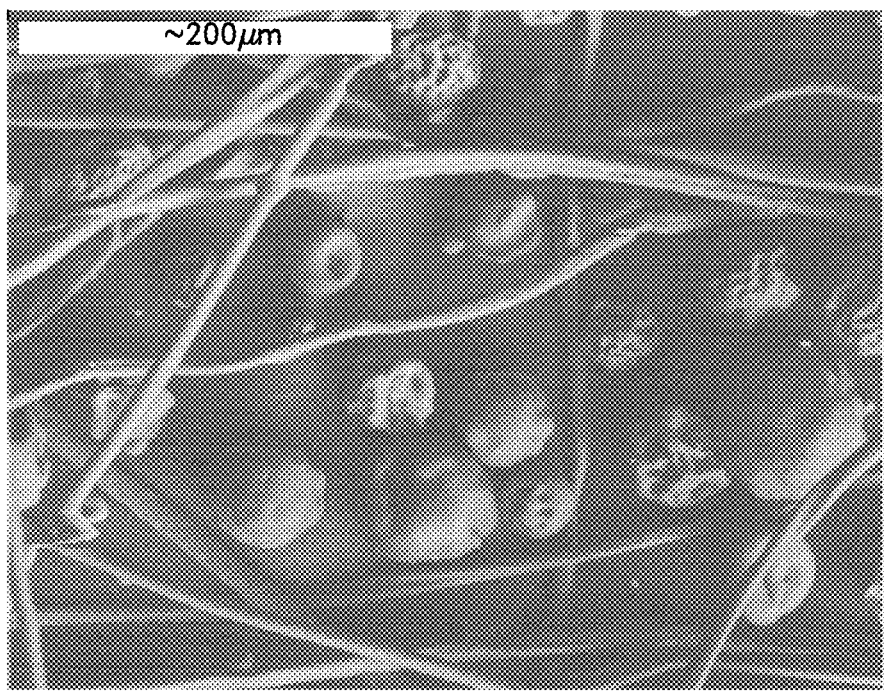
Figure 10C:
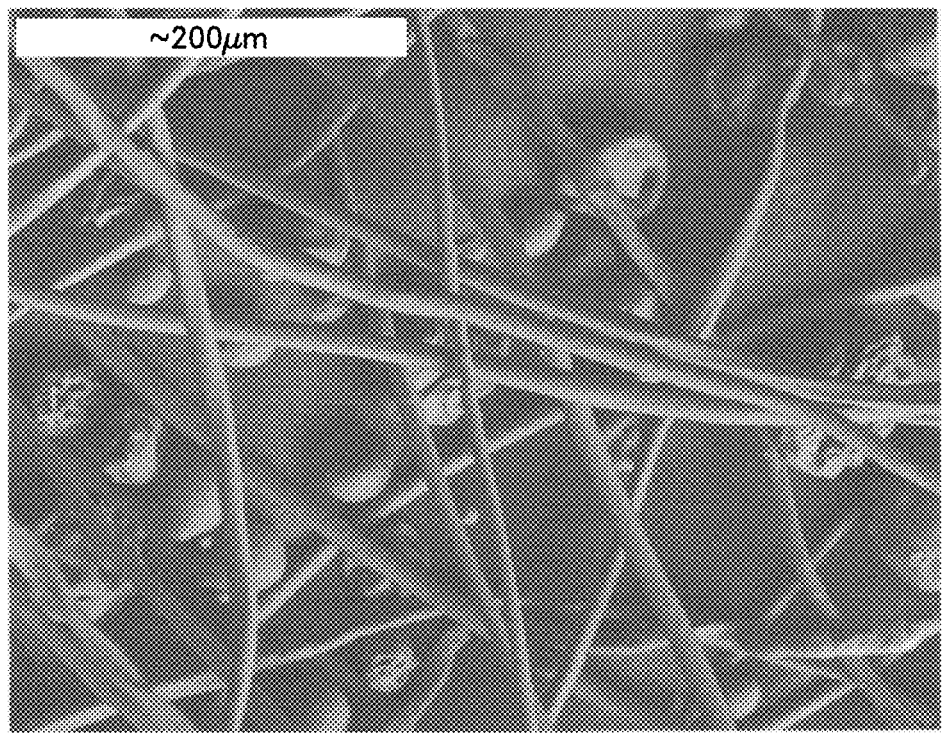

Microscopy of Chitosan Fleece Loaded with Microporous Polysaccharide Microspheres Chitosan fleece loaded with different amounts of microporous polysaccharide microspheres were examined using scanning electron microscopy. At 15% loading, uneven distribution of the microporous polysaccharide microspheres on chitosan fleece was observed (FIG. 7). At 60% loading, fewer microporous polysaccharide microspheres are observed (FIG. 8). It is believed that microporous polysaccharide microspheres were dislodged from the loaded chitosan fleece before or during the process of obtaining the SEM image. In the 60% loaded specimen, particulate microporous polysaccharide microspheres on the surface of the specimen container were observed. It is also possible that the microporous polysaccharide microspheres were removed by the vacuum used in the SEM sputter coating process to prepare the specimens. It is believed that when the loose microporous polysaccharide microspheres are deposited in the interstices of the chitosan fleece, some weak electrostatic bonding of the neutral or slightly acidic microporous polysaccharide microspheres to the cationic chitosan occurs. FIGS. 10A, 10B, and 10C provide SEM images of microporous polysaccharide microspheres physically loaded onto chitosan fleece. The loaded fleece was pressed onto a carbon sticky tape. As seen in the images, many of the spheres were dislodged during the process of transferring the loaded fleece onto the sticky tape, but retain their pore morphology.

Figure 9A:
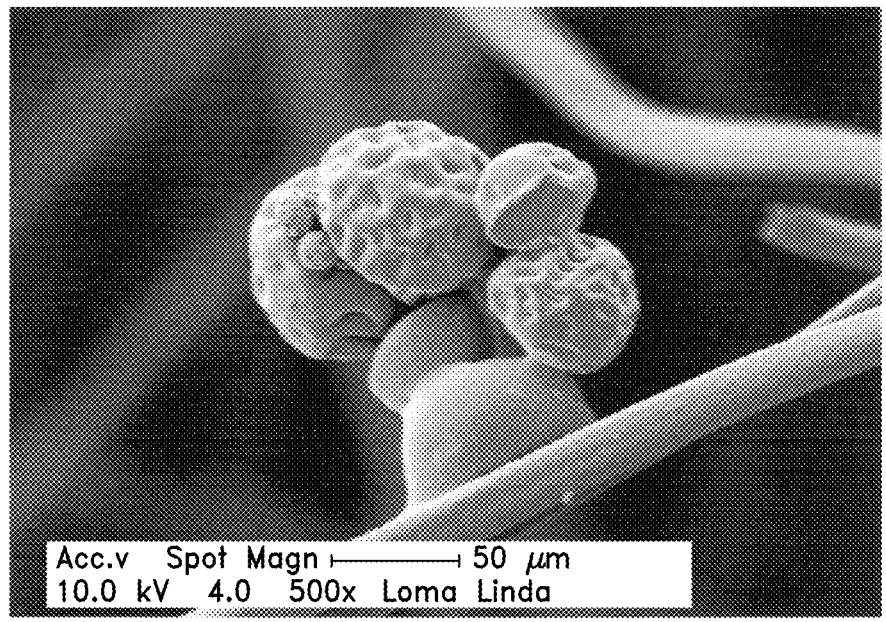
FIGS. 9A and 9B provide scanning electron micrographs of microporous polysaccharide microsphere clusters fused or bonded to chitosan fibers.
Figure 9B:
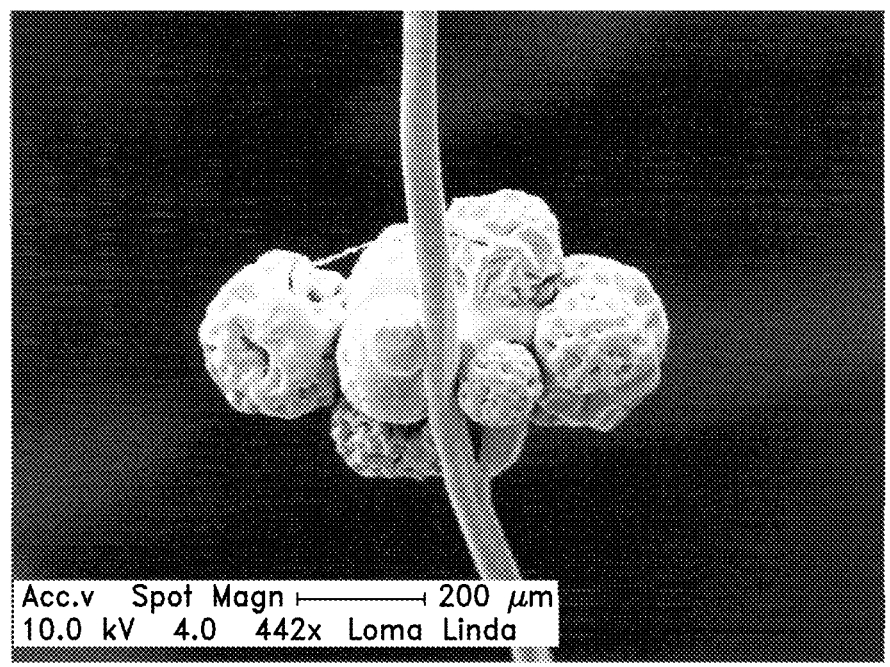

The attachment of the microporous polysaccharide microspheres to the strands of chitosan fleece was also observed. Some degree of melting or fusing of both the chitosan and microporous polysaccharide microspheres can also occur during the manufacturing process, resulting in a bond that can be visualized with scanning electron microscopy. It was observed that the microporous polysaccharide microspheres attach to the strands in clusters, with one or more microspheres fusing to the strand. These fused spheres generally exhibit a smooth surface and do not have the detailed pore structure of spheres in the clusters not directly attached to the strand. FIGS. 9A and 9B provide scanning electron micrographs of microporous polysaccharide microsphere clusters fused or bonded to chitosan fibers with loss of pore structure. Once the microporous polysaccharide microspheres lose their pores, as can occur during fusing or melting, their effectiveness as a procoagulant is significantly impaired.

By loading the microspheres onto the chitosan fleece by methods of the preferred embodiments, the microporous polysaccharide microspheres can be combined with the chitosan fleece without substantial modification of the individual components morphologic appearances. A more even distribution of microporous polysaccharide microspheres on the chitosan fleece can be achieved by applying the weak acid more evenly, e.g., applying the weak acid in a smaller droplet size, such as by an atomizer or spray jet, to chitosan fiber in a rotating drum, on a conveyor belt, or the like, optionally with a vacuum source applied to the chitosan fiber to pull the droplets into the mass of fiber, and/or an air blower to force the droplets into the mass of fiber. Tighter control of moisture levels during the coating process can also achieve better distribution of the microspheres, higher loading levels, or reduced impact on morphology of the fleece and microspheres.

In the procedures of the particularly preferred embodiments for preparation of chitosan fleece loaded with microporous polysaccharide microspheres, in order to avoid dissolution of the microspheres in aqueous solution and disruption of the microspheres' structure, only a small amount of acidic aqueous solution or glacial acetic acid is sprayed onto the surface of the chitosan fleece to maintain proper moisture levels. Consequently microporous polysaccharide microspheres are primarily "glued" onto the chitosan fleece.

While not wishing to be bound to any particular theory, is believed that chitosan fleece, optionally loaded with microporous polysaccharide microspheres, can have two primary mechanisms of action when employed in wounds. One is to stop bleeding very rapidly because microporous polysaccharide microspheres can rapidly absorb water in blood. Another is to repair the wound and any damaged blood vessels. The first action can cause the wound to stop bleeding instantly, while the second function can protect the wound and prevent secondary bleeding from damaged or cut blood vessels. It is believed that formation of a chitosan aqueous gel supported by moist chitosan fleece in the wound can contribute to the action.

Manufacturing Processes for Loading Chitosan Fleece

As discussed above, treating chitosan by carding or similar processes can create a layer of fleece which can be disposed on a conveyor belt for further processing. Such further processing can include loading the chitosan fleece with a polysaccharide, such as microporous polysaccharide microspheres or other polysaccharide agents and/or hemostatic agents. In one embodiment, a method of loading chitosan fleece with microporous polysaccharide microspheres comprises coating the fleece with an acid, such as glacial acetic acid, optionally followed by a process of applying a polysaccharide powder or other auxiliary agent.

In an acid coating process, a weak acid is atomized then applied to chitosan fleece. This can be accomplished by any suitable method including, for example, ultrasonic atomization. The atomized acid comprises a mist or fog of acid which is passed through the chitosan fleece which rests on a conveyor. Preferably, the atomized acid mist is simultaneously blown onto the fleece by a fan and sucked through the fleece and conveyor by an extracting pump. As such, the volume of acid mist that passes through and coats the fleece can be closely controlled and the acid mist can be contained within the acid coating process area.

After the fleece has been acid coated, it can enter a powder application process area where powderized microporous polysaccharide microspheres or other powderized agents are loaded onto the fleece, if desired. Preferably, powderized microporous polysaccharide microspheres are disposed in a vibrating sieve and are simultaneously blown onto and sucked through the fleece and conveyor by a fan and extracting pump. As such, the volume of polysaccharide powder applied to the fleece can be tightly controlled and the polysaccharide powder can be substantially contained within the powder application process area.

Preferably, the acid coating process area and powder application process area are substantially shielded from one another. After application of polysaccharide, the fleece preferably is delivered to a drying apparatus.

The method as described above provides a layer of fleece loaded with microporous polysaccharide microspheres. It is to be understood that further processing can be employed to incorporate such a layer into a nonwoven fabric in which several loaded fleece layers are attached to one another to make a nonwoven fabric of polysaccharide loaded chitosan fleece.

In accordance with one embodiment, a nonwoven fabric manufacturing process utilizes a drum about which a backing paper is wrapped. The backing paper preferably is coated with acid, such as glacial acetic acid or a weak acid solution, so that a base layer of loaded chitosan fleece sticks thereto. The base fleece layer is sprayed with another coating of acid, and another layer of loaded fleece is placed on the acid coated fleece. Due to the acid coating on the base layer, the fleece layers fuse with one another. This acid coating and fleece wrapping process can continue for as many layers of fleece as are desirable to create the nonwoven fabric. Once a suitable number of layers are formed, the fleece is removed from the cylinder and transported to a press, which exerts pressure against the fleece in order to further bind and compact the nonwoven fabric. In one embodiment, the fleece is dried within the press.

Chitosan with Deposited Starch

While not wishing to be bound by any particular theory, it is believed that the hemostatic efficiency of chitosan when combined with starch is much better than that of the chitosan or starch alone due to the formation of a new polymer wherein chitosan intercalates with the starch. Chitosan and starch have a similar structure and good mutual compatibility. The interpenetration and entanglement of chitosan and starch macromolecular chains is believed to occur when the polymers are blended with each other in a melting state or a plasticized state in the presence of an acidic aqueous solution. However, interpenetration and entanglement of two polymer chains are generally attributed to physical phenomenon that can alter certain physical properties of the original polymers while leaving their chemical structure unchanged. Consequently, interpenetrated and entangled polymers are regarded as a polymeric mixture or a polymeric composite, but not a new polymer. In chitosan, there are large numbers of amino groups ($-NH_2$) that are able to form hydrogen bonds with oxygen atoms in a carbonyl ($-C(O)-$), ester ($-COOR$), or ether ($-O-$) group. It is believed that hydrogen bonding exists between chitosan and starch polymeric chains. However, hydrogen bonding is generally classified as a physical interaction that does not change the chemical structure. Under certain conditions (such as heating, presence of a catalyst, and the like), an amino group can react with active aldehyde or ketone groups to yield a Schiff linkage, which is regarded as a chemical reaction. Creation of a Schiff linkage is generally not observed for the combination of chitosan and polysaccharide, since there are generally not enough active aldehyde and ketone groups in the polysaccharide to facilitate such linkages.

The rheology and microscopic topology of entangled polymeric liquids was reported by Everaers et al., Science, Vol. 303, 6 Feb. 2004, 823-826. It was found that the viscoelastic properties of high molecular weight polymeric liquids are dominated by topological constraints on a molecular scale. In a manner similar to that of entangled ropes, polymer chains can slide past but not through each other. Tube models of polymer dynamics and rheology are based on the idea that entanglements confine a chain to small fluctuations around a primitive path that follows the coarse-grained chain contour. A microscopic foundation for these phenomenological models is provided by Everaers et al., who analyze the topological state of polymeric liquids in terms of primitive paths, to obtain parameter-free, quantitative predictions for the plateau modulus, which agree with experimental data for all major classes of synthetic polymers.

As discussed by Viyoch et al., International Journal of Cosmetic Science, 25(3), 113 (2003), chitosan with a molecular weight of 100,000 and a starch such as corn, potato, or tapioca starch can be used in preparation of a cosmetic patch containing tamarind fruit extract. The physicochemical characteristics, i.e., flexibility, color, transparency, integrity, gloss, water sorption, bioadhesion property, and stability, of the patch without tamarind content were investigated. A stability test was performed by keeping the prepared patches at 4° C., at room temperature, or at 45° C. for two weeks. The results showed that the formulations composed of chitosan:corn starch ratio of 4.5:0.5 ($CC_{4.5:0.5}$) and chitosan:tapioca starch ratios of 4.5:0.5 ($CT_{4.5:0.5}$) and 4.0:1.0 ($CT_{4.5:1.0}$) provide patches with favorable physical characteristics, high water sorption, good bioadhesion ability and good stability. After the lyophilized tamarind extract in an amount corresponding to 5% of tartaric acid was incorporated into the formulations of $CC_{4.5:0.5}$, $CT_{4.5:0.5}$, and $CT_{4.5:1.0}$, the ability of the patches to adhere to skin was improved. However, after keeping the test patches at room temperature or at 45° C. for 6 weeks, their colors were intensified while their flexibilities and skin adhesion properties decreased. A 12 hour in vitro permeation test was conducted by observing the cumulative amount of tartaric acid permeated through the Silastic® membrane (Dow-Corning, Midland, Mich.). The $CC_{4.5:0.5}$ patch tended to give the highest amount of tartaric acid released. The release pattern of all the blended polymeric matrices was exhibited in two distinct phases: the rapid phase, wherein the flux averaged 3.61 µg $min^{-1}$ $mm^{-2}$; and the slow phase, wherein the flux averaged 1.89 µg $min^{-1}$ $mm^{-2}$. The methods described by Viyoch et al. for preparing blends of chitosan and starch can be adapted for preparation of chitosan substrates or hemostatic agents suitable for use in preparation of materials of preferred embodiments.

Chitosan with Deposited Dextran

Superior coating can be achieved by providing the chitosan fibers with a dextran coat having a microporous surface, rather than by depositing microporous polysaccharide microspheres. Such a dextran coating can be prepared in any number of ways. For example, dextran can be solubilized in water or a mild acid solution to confer electronegativity to the molecules by mild oxidation, whereby carboxyl groups are created. The dextran can also be reacted under controlled conditions to entangle the polymers. The chitosan dextran mixture can be lyophilized to create a surface that has microporosity on the chitosan fibers. The degree of dextran coating can be controlled, the thickness of the coating can be controlled, and the porosity size can be controlled by the various contributions of either a straight or branched chain amylose or amylopectin. A chemical bonding can take place with the reaction of a negatively charged dextran and the cationic chitosan. All of these processes can be monitored by both light and electron microscopy as well as by histochemistry of sections of the material to determine whether successful bonding has been achieved.

A variation of this technology involves preparing alternate layers of dextran-coated microporous chitosan and non-coated chitosan to prepare a gradient of a non-woven fleece and fabric. Methods known in the art for applying dextran coating to various substrates can be modified to yield methods of applying dextran coatings to chitosan fibers. Microporous polysaccharide microspheres can also exhibit superior adhesion to dextran-coated chitosan fibers. Accordingly, in certain embodiments it can be desirable to pretreat chitosan fibers with dextran prior to deposition of the microporous polysaccharide microspheres.

Chitosan-Microporous Polysaccharide Microsphere Production Process

The term "chitosan" corresponds to a family of polymers that vary in degree of N-deacetylation (DA). Chitosan generally varies from about 50 to 70% DA or higher with variable viscosity, solubility, and hemostatic properties. Since the behavior of chitosan polymers, namely their reactivity, solubility, and ability to bind MPH, depends on the DA of chitin and chitosan, an assay to determine DA is desirable. FTIR spectroscopy and C13 mass NMR spectroscopy are linked for chitosan assays. The technique used to determine the degree of acetylation of chitin and chitosan is preferably FTIR spectroscopy. FTIR spectroscopy has the advantage of being non-destructive, fast, extremely sensitive, user friendly, low priced, and applicable for both soluble and nonsoluble samples.

Prior to assay, all proteins and endotoxins are removed from the chitin as produced for clinical applications. Chitosan fibers are examined to determine their cross section, their tensile strength, breaking strength, loading strength, and their appearance. This industrial engineering process is utilized in the manufacture of chitosan fleece and chitosan sponge, as well as in the manufacture of chitosan fabric. The amount of saturation of microporous polysaccharide microspheres is tested in model systems to determine appropriate physical characteristics for three major types of bleeding.

Characterizing the Structure and Properties of the Chitosan Fiber

Established and on-line methods for measuring the crystal structure, size, chitin DA, average molecular weight, content of heavy metals, and toxicity of the chitosan fiber are employed. Characterization testing includes testing for fiber strength, pulling rate, mean fiber swelling as ratio of fiber diameter after absorption to that before absorption of distilled water, and pH. Chitosan having a DA of 50 to 80 wt. % or more is compared. Materials that are assayed include microporous polysaccharide microspheres, chitosan of varying DA, and chitosan-microporous polysaccharide microsphere materials. Measurements of water and blood absorption, rates of water and blood release, local retention (using gel strength), and screening tests for hemostasis are also conducted. Since erythrocyte polymerization (agglutination) is considered a major factor for chitosan-induced blood coagulation, a simple hemagglutination test can be used for rapid screening of the product.

Simple hemagglutination assays are known in the art. Chitosan, chitosan-microporous polysaccharide microsphere, and microporous polysaccharide microsphere compositions are prepared in stock solutions containing 2000 µg/ml of the material. A 10 fold dilution is used to achieve a final concentration of 1000, 100, 10, or 0.1 µg/ml in a volume of 0.2 ml in 0.9% NaCl (normal saline). Human red cells (obtained from a blood bank) are rinsed twice with Alsever's Solution and twice with 0.9% sodium chloride. Sodium chloride is used to circumvent incompatibility between deacetylated chitin and other ions. Washed red cell are suspended in a saline solution (0.9% NaCl) and adjusted to 70% transmission with a colorimeter (Klett-Summerson, No. 64 filter). An equal volume of red cell suspension (0.2 ml) is added to the various dilutions of chitosan-microporous polysaccharide microsphere, chitosan, and microporous polysaccharide microsphere compositions. Tubes are incubated for 2 hours at room temperature before reading. Deacetylated chitin (chitosan) normally produces hemagglutination of human red blood cells at a concentration of 1 µg/ml.

Protein binding capacity can be determined using biomedical sensors utilizing reflectometry interference spectroscopy (RIFS), that enables the kinetics of the absorption of proteins onto the surface of chitosan, chitosan-microporous polysaccharide microsphere, and microporous polysaccharide microspheres alone to be determined. Once an optimal chitosan-microporous polysaccharide microsphere is reached for hemostasis, batches can be quickly evaluated for protein binding capacity and this parameter related to hemostatic effectiveness in the rat model cited above.

Optimization of microporous polysaccharide microsphere loading to chitosan can be achieved using systems other than the acetic acid treatment for solution and loading microporous polysaccharide microspheres into the chitosan. Lactic acid can reduce more toxicity than acetic acid. The binding of microporous polysaccharide microspheres (starch), a non-polar polysaccharide to chitosan—a strongly cationic polysaccharide can conceivably be enhanced by selective starch oxidations and generation of an anionic state.

Studies of the degradation kinetics of chitosan fibers, chitosan fleece, and fabric, but with and without microporous polysaccharide microspheres are conducted. Studies of the hemostatic mechanism of chitosan-microporous polysaccharide microsphere fleece and fabric are conducted using multiphoton imaging and spectroscopy to evaluate the molecular interaction of chitosan, chitosan-microporous polysaccharide microsphere, and microporous polysaccharide microspheres with human and porcine whole blood and platelets. These results are compared to the determinations offered by application of NAG. In vitro clot formation, RBC aggregation, and platelet activation are studied.

Design and manufacture of a production line for large scale production of microporous polysaccharide microsphere mixed chitosan fleece and non-woven fabric is conducted. Machines to perform the following functions are developed to loosen the chitosan fiber; to card the loosened fiber into a thin fleece net; to moisten the chitosan fiber fleece by dilute acetic acid (or lactic acid) solution; to homogeneously load microporous polysaccharide microspheres onto the thin piece of moist chitosan fiber; to roll up the thin piece of microporous polysaccharide microsphere-loaded chitosan fiber on a reel; and to dry the fiber in a vacuum. A fully automatic or semi-automatic production line is designed and assembled to produce a standardized bulk quantity of chitosan-microporous polysaccharide microsphere fleece and nonwoven fabric. Tests of the density of varied fleece preparations are conducted to optimize interstice size and optimal fleece density for hemostasis. Similar tests are performed on collagen fleece.

Optimizing Chitosan-Microporous Polysaccharide Microsphere Formulations to Meet the Needs of Specific Hemorrhagic Diathesis Formulations are optimized using models that the military has defined for testing and comparative evaluation of chitosan-microporous polysaccharide microsphere materials. These models include the fatal aortic punch lesion and large venous and diffuse capillary bleeding in a liver injury models (swine). The model for remote closure of arterial catheterization lesions is taken from the literature and can be readily adapted to close lesions with chitosan-microporous polysaccharide microspheres. The oral bleeding model in the rabbit permits testing in a vascular organ system in an animal whose coagulation status can be readily modified (platelets, heparinization). This model has been tested with liquid chitosan as a hemostatic agent.

Animal Hemostatic Testing of the Chitosan-Microporous Polysaccharide Microsphere Fleece and Fabric Hemostatic tests have been performed on injured large vessels (e.g., catheterized canine femoral artery) under heparinization, and also to the lethal swine transection model (femoral artery, femoral vein), and the punctured rat femoral artery and vein model.

Catheterized Canine Femoral Artery

The model for control of brisk bleeding after arterial puncture and catheterization is the puncture of the canine femoral artery in heparinized animals. Three animals had an 11.5 French catheter placed for 4-6 hours in the femoral artery, then were heparinized with activated clotting times (ACT) 2-3 times normal, and were maintained at normotensive levels by IV fluid replacement. The indwelling arterial catheter was removed and a chitosan-microporous polysaccharide microsphere patch (2×2 cm) was immediately applied to the bleeding vessel with minimal pressure for 10 minutes. Videotapes documented these studies.

Tests were conducted on Dog Three having a weight of 25.7 kg; sex F; and coagulation time ACT 277 seconds. The catheter in the dog femoral artery was a 11.5 F catheter. 1-2 cm$^3$ of chitosan-microporous polysaccharide microsphere fleece was placed on the femoral artery puncture hole immediately after the 11.5 F catheter was removed. Manual pressure was applied on the fleece for 10 minutes and bleeding was completely stopped with absolute hemostasis. A chitosan-microporous polysaccharide microsphere patch was applied to a femoral vein puncture hole, another 11.5 F catheter was removed, and held with manual pressure for 7 minutes. Complete hemostasis was achieved. Venous pressure was increased by proximal ligation and the chitosan-microporous polysaccharide microsphere patch adhered without bleeding.

Tests were conducted on Dog Four having a weight of 25.4 kg; sex F; and coagulation time ACT 280 seconds. A 1-2 cm$^3$ chitosan-microporous polysaccharide microsphere patch was placed on the femoral artery puncture hole immediately after the 11.5 F catheter was removed, and manual pressure was applied for 10 minutes. Complete hemostasis with marked adherence of the fleece was noted.

Tests were conducted on Dog Five having a weight of 23.1 kg; sex M; and coagulation time ACT 340 seconds. PVA treated chitosan-microporous polysaccharide microsphere fleece (1 cm$^3$) was applied to the femoral artery puncture hole after the 11.5 F catheter was removed and manual pressure was applied for 10 minutes. Bleeding stopped, but 30 seconds later moderate bleeding from the puncture wound was noted. A second attempt using the same PVA treated chitosan-MPH fleece (with 10 minutes manual compression) failed. Chitosan-MPH non-woven fabric without PVA was then used to replace the relatively non-adherent PVA treated chitosan-MPH fleece. Complete hemostasis was achieved after 15 minutes of manual compression. The wound was observed for 20 minutes and no bleeding was noted. The non-PVA treated chitosan-MPH fabric adhered tightly to the artery and surrounding tissue. Artery with fabric was removed for pathology.

The dog experiments demonstrated that chitosan-microporous polysaccharide microsphere fleece (non-PVA treated) was remarkably effective as a hemostatic agent in the heparinized canine arterial catheterization model. Large bore catheter (11.5 F), left in place for 4-6 hours results in a significantly molded, vascular breech and in the face of significantly prolonged coagulation time represents a substantial hemostatic challenge. Chitosan-MPH fleece also conforms to the arterial contour, does not interfere with distal flow, and is remarkably adherent. Chitosan-microporous polysaccharide microsphere fleece was equally effective in achieving hemostasis in the catheterized femoral vein and was also remarkably adherent without interfering with flow. Chitosan-microporous polysaccharide microsphere fleece (PVA treated) achieved moderate to minimal hemostasis in one trial, and was relatively non-adherent. Complete hemostasis was secured with a non-PVA treated chitosan-MPH fabric patch.

Rat Punctured Femoral Artery and Vein

Femoral arteries and veins of three rats (OD 1.5 to 2 mm) were exposed bilaterally after barbiturate anesthesia was achieved. Puncture wounds were made in each artery with a 30 gauge needle, and a pledget (3 mm$^3$) of chitosan-microporous polysaccharide microsphere fabric was placed on the puncture site for 10 seconds and monitored for bleeding. PVA treated material was not used. Control of bleeding from the injured thin walled rat femoral vessel for 100 min. is a hemostatic challenge. After exposing both femoral arteries, a 30 gauge needle was used to puncture the arteries to create an arterial laceration and brisk bleeding.

Tests were conducted on Rat No. 1, a male weighing 520 g. The right femoral artery puncture wound was treated with a pledget of chitosan-microporous polysaccharide microsphere fabric. Gentle compression was applied to the pledget for 30 seconds, and after release there was very slight bleeding under the fabric. Gentle manual pressure was applied again for 10 seconds and the bleeding completely stopped. After 20 minutes observation of complete hemostasis, both proximal and distal ends of the femoral artery were ligated and a burst strength test was conducted. The fabric repaired wound remained intact at 120 mm Hg.

Tests were conducted on Rat No. 2, a male weighing 525 g. The left femoral artery puncture wound was treated with a 3 mm$^2$ pledget of chitosan-microporous polysaccharide microsphere fabric. Manual compression was applied on the fabric for 10 seconds. After release of manual pressure there was slight bleeding under the fabric patch. 2 seconds of additional manual pressure was applied but minimal bleeding continued at a diminishing rate. No additional pressure was applied and bleeding stopped completely after 56 seconds. After 20 minutes of complete hemostasis both proximal and distal end of the femoral artery were ligated and the burst strength test was conducted. Chitosan-microporous polysaccharide microsphere fabric repaired wound withstood arterial pressure until 300 mm Hg. The right femoral artery puncture wound was treated by placement of a fat pad over the injury. Manual compression was applied on the fatty tissue for 10 seconds. After release of the manual pressure there was profuse bleeding under the fatty tissue. No additional pressure was applied. The bleeding stopped after one minute and 27 seconds and 20 minutes later both proximal and distal end of the femoral artery were ligated and a burst strength test was conducted. The fatty tissue repaired wound failed at approximately 60 mm Hg.

Tests were conducted on Rat No 3, a male weighing 555 g. A right femoral artery puncture wound was treated with a chitosan-microporous polysaccharide microsphere 3 mm$^2$ pledget mixed chitosan non-woven fabric used to cover the wound. Manual compression was applied for 20 seconds, and after release complete hemostasis was secured. After 20 minutes of observation, both proximal and distal ends of the femoral artery were ligated and a burst strength test conducted. The chitosan-microporous polysaccharide microsphere patch withstood arterial pressure until 200 mm Hg. The right femoral artery puncture wound was covered with fatty tissue. Manual compression was applied on the fatty tissue for 20 seconds and after release of the manual pressure there was profuse bleeding. Bleeding stopped after one minute and 21 seconds with continued manual pressure. After that, both proximal and distal ends of the femoral artery were ligated and a burst strength test was conducted. The fatty tissue patch failed at less than 120 mm Hg (approx. 60).

The rat tests demonstrated that chitosan-microporous polysaccharide microsphere pledgets were remarkably effective in achieving complete hemostasis in the face of brisk bleeding from a puncture wound in a fragile vessel. The time required for the chitosan-microporous polysaccharide microsphere fabric to stop bleeding varied from 20 seconds to 56 seconds. This could be caused by an uneven distribution of microporous polysaccharide microspheres on the chitosan non-woven fabric patch. The chitosan-microporous polysaccharide microsphere patch adheres very tightly to the vessel and can withstand high arterial pressures before failing. The rat femoral artery puncture model is an excellent screening system to study mechanisms for hemostasis and tissue adherence as well as screening of various chitosan-microporous polysaccharide microsphere formulations.

Swine Femoral Artery and Femoral Vein

Tests were conducted wherein a lethal large artery injury transects the femoral artery and femoral vein. The chitosan-MPH puff provided remarkable hemostasis in comparison to other methods that were utilized.

Fatal Aortic Injury Model in the Pig

This model was developed for hemostatic agent testing conducted at the U.S. Army Institute of Surgical Research, San Antonio, Tex., for the purpose of determining the optimal hemostatic dressing for high pressure arterial bleeding. The injury is a calibrated puncture hole in the distal aorta of normotensive pigs. Nine different hemostatic dressings were evaluated for this otherwise 100% fatal injury. The only animals that lived 60 minutes received the American Red Cross Fibrin Dressing (Fibrin and Thrombin) or had suture repair of the lesion. All other hemostatic agents to include NAG failed to control the aortal hemorrhage and no animals survived 60 minutes. Chitosan and microporous polysaccharide microsphere were not included in these experiments.

Five groups of five pigs (40 kg, immature Yorkshire cross swine male) restudied. One group is treated with American Red Cross Fibrin Dressing, the other four groups with chitosan fabric with or without microporous polysaccharide microspheres and chitosan fleece with or without microporous polysaccharide microspheres. Microporous polysaccharide microspheres alone generally do not control brisk arterial bleeding and are not included. Previous experiments demonstrated the fatality of the lesion untreated and that the animals can be rescued by suture repair. The objective of this study is to compare the American Red Cross Dressing to chitosan-based dressings. Survival, blood loss, and amount of IV resuscitatable fluid to maintain normotension are determined.

Animals are premedicated (Telazol 4-6 mg/kg IM, Robinul 0.01 mg/kg 1M), endotracheal anesthesia is maintained with 1-3% isofluorane and oxygen, and core temperature held between 37°-39° C. Indwelling arterial lines are placed for both proximal (carotid) and distal (femoral) MAP (Mean Arterial BP determinations) and a femoral IV line is inserted for resuscitative fluid administration. Pigs are spelenectomized, the spleen weighed, and replacement fluid (3× splenic weight of warm lactated Ringers) solution administered to correct for blood removal (spleen).

Hemodynamic stabilization is secured after splenectomy within 10 minutes and arterial blood samples (12 ml) are obtained prior to the aortic punch. The aortic injury is made immediately after aortic occlusion and arterial blood is drawn 30 and 60 minutes after the injury. Prothrombin time, activated partial thromboplastin time, fibrinogen concentration, thromboelastogram, complete blood count, lactate, and arterial blood gases are determined.

After the splenectomy and 10 minute stabilization period, drains to continuous suction are positioned bilaterally in the lateral abdominal recesses. Rate of bleeding is determined by weighing the blood loss over time and is expressed as grams accumulated per 10 seconds. After cross clamping the aorta above and below the site of the injury, (3 cm above the bifurcation of the distal aorta, aortotomy made with a 4.4 mm aortic hole punch) cross clamps are removed. Bleeding is initially tamponaded by placing a finger on the hole without vessel compression. At 0 time the finger relieves the tamponade and brisk arterial bleeding is allowed for 6 seconds. Blood is collected and rate of blood loss monitored by deflecting blood into the peritoneal cavity for drainage.

A polyethylene elastic sheet is placed between the dressing and gloved hand and after 6 seconds of brisk bleeding the test hemostatic dressing is applied for four minutes. Manual compression consists of complete aortal occlusion as manifested by a non-pulsatile femoral BP (MAP at 15 mm Hg). After four minutes, manual compression is relieved leaving the dressing and plastic sheet over the injury site. The injury site is observed for bleeding for two minutes. A key endpoint is a complete absence of bleeding after 2 minutes of observation. If bleeding persists, another four minutes of compression is administered. In the event of active bleeding or no hemostasis, resuscitation is discontinued and the animal is allowed to die. In order to test the adherence of the test dressing with no evidence of bleeding, resuscitation is instituted with 37° C. lactated Ringer solution at a rate of 300 ml/min IV. A pre-aortotomy baseline MAP plus or minus 5 mm Hg is maintained for an additional 60 minutes. Death (a key endpoint) is a MAP<10 mm Hg and end tidal PCO2 less than 15 mm Hg. At the end of the experimental period (euthanasia at 1 hour in surviving animals) aortas are removed, opened, and evaluated. After the lesion is observed and photographed the size of the hole is measured to ensure uniformity of injury size, and the specimen fixed for histological examination to evaluate the hemostatic process (fibrin, platelets, extension into lumen).

Though the ARC hemostatic dressing has provided survival in this model it still has disadvantages. The "ideal" hemostatic dressing, in addition to the parameters cited earlier, controls large vessel arterial venous and soft tissue bleeding, adheres to the vessel injury but not to the glove or hands, is flexible, durable, inexpensive, stable in an extreme environment, has a long shelf life, does not require mixing, poses no risk of disease transmission, does not require new training, and is manufactured from readily available materials. None of the dressings that have been tested or evaluated in the current setting meet all of these characteristics. The shortcoming of the fibrin-thrombin American Red Cross field dressing (ARC) is that it is fragile in its current form. The field dressing is stiff and thick when dry and some of the lyophilized material flakes off when the field dressing is grasped. The fibrin-thrombin dressing sticks to latex gloves and skin when wet. The handling characteristics of the chitosan fleece with MPH are superior to these prior art materials.

The Canine Femoral Artery Catheterization Model

Extensive background literature for the evaluation of this novel vascular sealing device exists. Femoral arteries are studied by percutaneous placement of standard vascular sheaths (7 French) with catheters inserted by the Seldinger technique. A total of twenty animals are utilized, ten anticoagulated with IV heparin 150 units/kg to activated clotting times (A.C.T.) 3× normal. The ACT is measured just prior to insertion of the sealing device. Unheparinized animals have the contralateral femoral artery used as a control with only manual compression used to achieve hemostasis. Arterial sheaths and catheters are left in place for one hour to simulate an intervention duration. The vascular sealing device with the chitosan-MPH in one femoral artery and manual compression are utilized on the other femoral artery. Manual pressure applied to the puncture site is released and the puncture site is inspected every five minutes for the following key endpoints: external bleeding or hematoma formation, measurement of thigh circumference, integrity of the distal pedal pulses, and manual compression time required to achieve hemostasis. Animals are observed for an additional ninety minutes, then euthanized with an overdose of IV sodium pentobarbital and saturated potassium chloride. Prior to euthanization, animals are subjected to femoral angiography in each group.

A subgroup of animals survive with a follow-up examination at 2 weeks. This includes physical inspection of the arterial access, assessment of the distal pulses, femoral angiography, and histopathologic examination of the excised femoral artery puncture site and surrounding tissue. Statistical analysis is expressed as mean standard deviation. The student's t-test unpaired is used for comparing the mean times to hemostasis within the different treatment groups. Preliminary animal studies are performed before proceeding to human clinical trials. Chitosan fleece with microporous polysaccharide microspheres and chitosan fabric with microporous polysaccharide microspheres both exhibit superior performance in controlling blood loss as well as the other parameters tested.

Model for Severe Large Venous Hemorrhage and Hepatic Injury (Swine)

This model has been extensively tested by the U.S. Army Combat Casualty Care Research Program. There is a large baseline of data regarding extent of injury and response to a variety of hemostatic agents. This data includes documentation of the extent of injury to large diameter veins, ability to apply hemostatic dressings in the face of massive bleeding, extent of blood loss, facility of instrumentation, lethality, and reproducibility of the experimental liver injury. Both the American Red Cross Hemostatic Dressing (ARC) and the experimental chitosan acetate sponge proved to be effective hemostatic agents in this model. The military investigators concluded that both the chitosan and American Red Cross Dressing (ARC) warranted further studies and development. The hemostatic effectiveness of chitosan (fleece, fabric, with or without microporous polysaccharide microspheres) and the ARC dressing in the pig severe large venous hemorrhage model was tested. The recommended conventional therapy for treating Grade V hepatic injuries (extensive parenchymal damage combined with major vascular lacerations) is tamponade with gauze sponges and later reoperation. The issue of biodegradability and wound healing has never been resolved with these hemostatic agents. Consequently surviving animals are sacrificed one month post-injury to examine the healing wound and hemostatic agent degradation. Hemostatic control is monitored over the one-month period by weekly hepatic CT scans. Evidence of rehemorrhage requires intervention laparotomy and animal sacrifice. The post-injury and hemostatic repair course of the animals is monitored.

Crossbred commercial swine (males, 40-45 kg) are divided into six groups of five animals each. Test groups consist of gauze packing, ARC dressing, chitosan fleece with or without microporous polysaccharide microspheres and chitosan fabric with or without microporous polysaccharide microspheres. Surgical preparation and anesthesia is as for the aortic punch injury model. Carotid artery and jugular vein lines are placed, and splenectomy and urinary bladder catheter placement completed. Both hemodynamic (stable MAP for 15 minutes) and metabolic (rectal temperature 38-40° C., arterial blood pH 7.39-7.41) stabilization are achieved. Arterial blood samples are obtained. Each test animal must have a normal hematocrit, hemoglobin concentration, platelet count, prothrombin time, activated partial thromboplastin time, and plasma fibrinogen concentration to be included in the study. Drains are placed bilaterally (as in the aortotomy) for rate and quantitative blood loss calculation. The liver injury is induced exactly as described in previous publications. Essentially, a specially designed clamp, "X" shaped, consisting of 4.5 cm sharpened tines and a base plate is used to make two penetrating liver lacerations. The standardized liver injuries are through-and-through stellate wounds, involving the left medial lobar vein, right medial lobar vein, portal hepatic vein, and hepatic parenchyma. Thirty seconds after injury, warm (39° C.) lactated Ringer's solution is started at a rate of 260 ml/min to restore the baseline MAP (Mean Arterial Pressure). The experimental hemostatic dressings are applied at the same time as IV fluids are initiated with manual compression via standardized applying pressure in a dorso-ventral direction. After one minute, the wound is inspected for bleeding. If hemostasis is not complete, pressure is reapplied in the lateromedial direction. The sequence is repeated four times, with 60 seconds of compression. The key endpoints of hemostasis are defined as the absence of any detectable bleeding from the injury. After application of the hemostatic treatment, the animals' abdomen is temporarily closed and the animal observed for 60 minutes. The endpoint for death is a pulse of 0. Quantitative blood collection prior to treatment application is termed "pretreatment blood loss," at the end of the study period this is referred to as the "post-treatment blood loss." Blood in the hemostatic agents is not included but total IV fluid replacement and estimated pre-injury blood volume is determined.

Adherence strength of the hemostatic dressing is estimated using the subjective scoring system reported by the military team who devised this protocol. Scores range from 1 to 5; 1=no adherence, 2=slight, 3=adherence to cause stretching of tissue in contact with hemostatic agent but not lifting liver from table, 4=adherence sufficient to partially lift liver from table, and 5=sufficient adherence to lift liver from table. The mean score for the 3 dressings from each animal is treated as a single value for adherence strength.

Key endpoints are survival, death, pretreatment blood loss, post-treatment blood loss, survival time, hemostasis at 1, 2, 3, or 4 minutes, % resuscitation fluid volume, (no values for adherence data given). Key parameters of injury are number of vessels lacerated correlated with pre-treatment blood loss in ml and ml/kg body weight.

Chitosan fleece with microporous polysaccharide microspheres and chitosan fabric with microporous polysaccharide microspheres both exhibit superior performance in controlling blood loss as well as the other parameters tested.

Oral Bleeding Model: Lingual Hemostasis in the Rabbit

This model provides convenient hemostatic testing in a system with enhanced capillary blood flow (the tongue) and high fibrinolytic activity (oral mucosa). This model can easily have platelet function suppressed as well as be heparinized. The model has been used to evaluate the hemostatic effect of liquid chitosan in dilute acetic acid with the key endpoints of a reduced bleeding time after a standard incision. Descriptions of the model have been published and provide baseline data for the results to be compared.

The hemostatic effectiveness of NAG, considered highly hemostatic for capillary hemorrhage, is compared with chitosan fleece with and without microporous polysaccharide microspheres and chitosan fabric with and without microporous polysaccharide microspheres. The key endpoints are lingual bleeding time, measured in minutes from the time the hemostatic agent is applied until hemostasis is complete. Rabbits are euthanized one to fourteen days after the surgery and the lesions evaluated histologically. Rabbits with normal blood coagulation status, suppressed platelet activity, and heparin anticoagulation are studied. NZW rabbits, 5-6 lbs, are studied for lingual hemostasis after using the model developed by Klokkevold, et al., consisting of a special metal stent sutured to the tongue in order to stabilize soft tissues and insure a consistent injury. Tongue incisions on the lateral border are made with a guarded 15 blade knife. Bleeding time measurements from the incision are made using the filter paper procedure of Coles. Blots are taken every 15 seconds until no blood staining occurs. Systemic bleeding and coagulation times are also determined. A total of 30 rabbits are studied, six groups of five each. The six groups consist of control (no treatment), NAG, chitosan fleece with or without microporous polysaccharide microspheres, and chitosan fabric with or without microporous polysaccharide microspheres. After animals are anesthetized (IM Ketamine HCl 35 mg/kg and Xylazine 5 mg/kg) an ocular speculum is inserted into the mouth to hold it open and the stainless steel stent sutured to the tongue to stabilize tissues. Tongue incisions are made with a depth of 2 mm, length 15 mm on the lateral border of the tongue with a guarded 15 blade. Incisions are immediately treated with the hemostatic agents and bleeding times measured. The method of tongue marking prior to incision is utilized to facilitate histologic sectioning post-marker. The identical study as above in 30 rabbits, five groups of five each, is conducted in animals treated with a platelet function antagonist—epoprostanol (prostacyclin or $PGI_2$). The protocol of Klokkevold is followed explicitly. Again, 30 rabbits are studied after the activated coagulation time has been prolonged 3× as well as increasing the mean systolic bleeding time by 40%. The histological exam is to include SEM. Chitosan fleece with MPH and chitosan fabric with MPH both exhibit superior performance in controlling oral bleeding.

Swine Tests—Lethal Groin Injury Model 1.5 g of chitosan fleece loaded with microporous polysaccharide microspheres was tested in one swine (94 kg) in the lethal groin injury model developed by Dr. Hasan Alam, a trauma surgeon and research specialist in the area of battlefield casualties who is on the staff of the Washington (DC) Hospital Center and serves on the faculty of the Uniformed Services University of the Health Sciences (USUHS). After severing the femoral vessels, bleeding was allowed to continue until the animal had lost blood equivalent to approximately 20 to 25 ml/kg of body weight. By allowing a fixed amount of blood loss based on body weight rather than bleeding for a specific time, a more consistent pathology is created. After the fixed amount of blood loss, a 1.5 g piece of chitosan fleece was placed on the wound. The chitosan fleece was successful in controlling the bleeding from the severed vessels. Following resuscitation with 500 ml of Hespan, the animal was observed until the mean arterial pressure had stabilized at approximately 45 mm Hg. No bleeding was observed in this observation period. At that time, additional resuscitation plus calcium and dopamine were administered to increase the mean arterial pressure to 95 mm Hg with no indication of bleeding. The animal was sacrificed and the fleece was examined.

Altered chitosan fleece was tested on another swine (87 kg). The chitosan fleece was altered by adding additional microporous polysaccharide microspheres to the fleece to compensate for any loss of microporous polysaccharide microspheres during the alteration. The application was successful and after approximately one hour the mean arterial pressure was increased using Hespan and dopamine to stress the application. No bleeding was observed until the mean arterial pressure was raised to approximately 95 mm Hg, at which time bleeding resumed. The fleece was removed. The material was observed to be stiff and hard. An additional fleece was placed in the wound. After that, the bleeding was controlled. The additional fleece was unaltered chitosan fleece containing microporous polysaccharide microspheres.

Both of these applications demonstrated that to achieve satisfactory control of strong bleeding, it is necessary to place the fleece on the injured vessel. Little bleeding occurs in the bottom of the femoral wound. If the material is placed in the bottom of the wound, bleeding may not be controlled. Accordingly, the material is preferably carefully placed in the wound so as to contact the femoral artery. Overall, the applications were very successful and suggested that when properly applied the formulations have good efficiency.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. All patents, applications, and other references cited herein are hereby incorporated by reference in their entirety.

What is claimed is:

1. A hemostatic material, the material comprising a plurality of layers of chitosan fibers, the chitosan fibers secured to each other to form a net structure by treatment with a glacial acetic acid or a weak acid solution of pH 3.0 to 4.5, wherein surfaces of the chitosan fibers are further treated by application of glacial acetic acid to form ammonium salt of chitosan.

2. The hemostatic material of claim 1, wherein the weak acid is acetic acid.

3. The hemostatic material of claim 1, wherein the material is a nonwoven fabric.

4. The hemostatic material of claim 3, wherein the nonwoven fabric has a rough side and a smooth side.

5. The hemostatic material of claim 3, wherein both sides of the nonwoven fabric are rough.

6. The hemostatic material of claim 3, wherein the fabric comprises from 2 to 25 layers.

7. The hemostatic material of claim 1, wherein the chitosan fibers are of uniform thickness.

8. The hemostatic material of claim 1, wherein the chitosan fibers are of a mixture of thicknesses.

9. A process for preparing a hemostatic material, comprising:
    a) providing a first layer of chitosan fibers; and
    b) applying a glacial acetic acid or a weak acid solution of pH 3.0 to 4.5 to the layer of chitosan fibers, wherein surfaces of the chitosan fiber are further treated by application of glacial acetic acid to form ammonium salt of chitosan; and thereafter
    c) placing a second layer of chitosan fibers atop the first layer of chitosan fibers,
    a hemostatic material according to claim 1 is obtained.

10. The process of claim 9, wherein steps a) through b) are repeated at least once.

11. The process of claim 9, further comprising:
    heating the hemostatic material, whereby a liquid is vaporized from the hemostatic material.

12. The process of claim 9, further comprising:
    d) compressing the hemostatic material between a first surface and a second surface; and
    e) heating the hemostatic material, whereby a dry hemostatic material is obtained.

13. The process of claim 9, wherein the weak acid solution is an acetic acid solution.

* * * * *